United States Patent
Conley et al.

(10) Patent No.: US 12,195,774 B2
(45) Date of Patent: Jan. 14, 2025

(54) ANTIDOTES TO FACTOR XA INHIBITORS

(71) Applicant: Alexion Pharmaceuticals, Inc., Boston, MA (US)

(72) Inventors: Pamela B. Conley, Palo Alto, CA (US); Genmin Lu, Burlingame, CA (US); Leonard G. Presta, San Francisco, CA (US); John T. Curnutte, Tustin, CA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 847 days.

(21) Appl. No.: 17/254,146

(22) PCT Filed: Jun. 18, 2019

(86) PCT No.: PCT/US2019/037726
§ 371 (c)(1),
(2) Date: Dec. 18, 2020

(87) PCT Pub. No.: WO2019/246094
PCT Pub. Date: Dec. 26, 2019

(65) Prior Publication Data
US 2021/0371842 A1    Dec. 2, 2021

Related U.S. Application Data

(60) Provisional application No. 62/686,968, filed on Jun. 19, 2018.

(51) Int. Cl.
*C12N 9/64* (2006.01)
*A61K 38/00* (2006.01)

(52) U.S. Cl.
CPC ........... *C12N 9/6432* (2013.01); *A61K 38/00* (2013.01); *C12Y 304/21006* (2013.01)

(58) Field of Classification Search
None
See application file for complete search history.

(56) References Cited

U.S. PATENT DOCUMENTS

| 8,153,590 B2* | 4/2012 | Lu | A61K 47/60 |
| | | | 435/325 |
| 8,268,783 B2* | 9/2012 | Sinha | A61K 38/4853 |
| | | | 424/94.64 |
| 2009/0098119 A1* | 4/2009 | Lu | A61K 38/4826 |
| | | | 435/69.6 |
| 2010/0125052 A1 | 5/2010 | Lu et al. | |
| 2010/0255000 A1 | 10/2010 | Sinha et al. | |
| 2015/0376592 A1 | 12/2015 | Lu et al. | |
| 2017/0369862 A1 | 12/2017 | Karbarz et al. | |

FOREIGN PATENT DOCUMENTS

| JP | 2014-197719 A | 10/2014 |
| WO | WO 2009/042962 A2 | 4/2009 |
| WO | WO 2010/056765 A2 | 5/2010 |
| WO | WO 2010/065293 A1 | 6/2010 |
| WO | WO 2013/123248 A1 | 8/2013 |

OTHER PUBLICATIONS

Stryer, Biochemistry 4th, WH Freeman, New York. 1995 (Year: 1995).*
Brown, Mark A. et al. "Coagulation Factor Xa." Handbook of Proteolytic Enzymes (2013): 2908-2915. doi:10.1016/B978-0-12-382219-2.00642-6 (Year: 2013).*
Augustsson, et al. Factor Xa and VIIa inhibition by tissue factor pathway inhibitor is prevented by a monoclonal antibody to its Kunitz-1 domain. J Thromb Haemost. May 2018; 16(5):893-904.
International Search Report and Written Opinion dated Dec. 4, 2019 for PCT/US2019/037726. (13 pages).
Spevak, et al. Sequence requirements for ribosome stalling by the arginine attenuator peptide. J Biol Chem. Dec. 24, 2010;285(52):40933-42.
Wood, et al. TFPIα interacts with FVa and FXa to inhibit prothrombinase during the initiation of coagulation. Blood Adv. Dec. 26, 2017;1(27):2692-2702.
European Search Report and Opinion dated Aug. 1, 2022 for EP Application No. 19822521.1. 16 pages.
Soenderkaer et al. Effects of sucrose on rFVIIa aggregation and methionine oxidation. European Journal of Pharmaceutical Sciences. vol. 21, Issue 5, Apr. 2004, pp. 597-606.

* cited by examiner

*Primary Examiner* — Michael Szperka
*Assistant Examiner* — Lia E Taylor
(74) *Attorney, Agent, or Firm* — Sheppard Mullin & Hampton LLP

(57) ABSTRACT

The present disclosure relates to antidotes to anticoagulants targeting factor Xa. The antidotes are factor Xa protein derivatives that bind to the factor Xa inhibitors thereby substantially neutralizing them but do not assemble into the prothrombinase complex. In one embodiment, the derivatives described herein lack or have reduced intrinsic coagulant activity.

4 Claims, 2 Drawing Sheets
Specification includes a Sequence Listing.

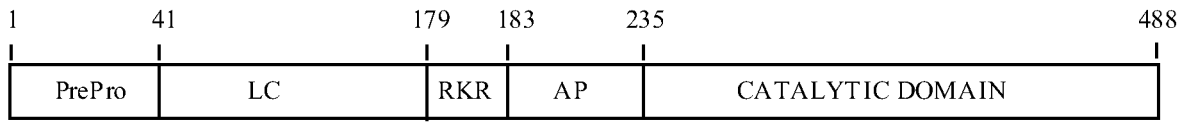

FIG. 1

```
                  10          20          30          40          50          60
                   |           |           |           |           |           |
Light Chain   1  ANSFLEEMKK  GHLERECMEE  TCSYEEAREV  FEDSDKTNEF  WNKYKDGDQC  ETSPCQNQGK
                              GLA DOMAIN(1-45)                    |
             61  CKDGLGEYTC  TCLEGFEGKN  CELFTRKLCS  LDNGDCDQFC  HEEQNSVVCS  CARGYTLADN
                         EGF1(46-84)                |          EGF2(85-128)
            121  GKACIPTGPY  PCGKQTLER
Heavy Chain                              SVAQATSS  SGEAPDSITW  KPYDAADLDP  TENPFDLLDF
                                (RKR)               ACTIVATION PEPTIDE
            181  NQTQPERGDN  NLTRIVGGQE  CKDGECPWQA  LLINEENEGF  CGGTILSEFY  ILTAAHCLYQ
                                                                            HIS236(H57)
            241  AKRFKVRVGD  RNTEQEEGGE  AVHEVEVVIK  HNRFTKETYD  FDIAVLRLKT  PITFRMNVAP
                                                                ASP282(D102)
            301  ACLPERDWAE  STLMTQKTGI  VSGFGRTHEK  GRQSTRLKML  EVPYVDRNSC  KLSSSFIITQ
            361  NMFCAGYDTK  QEDACQGDSG  GPHVTRFKDT  YFVTGIVSWG  EGCARKGKYG  IYTKVTAFLK
                             SER379(S195)
            421  WIDRSMKTRG  LPKAKSHAPE  VITSSPLK
```

FIG. 2

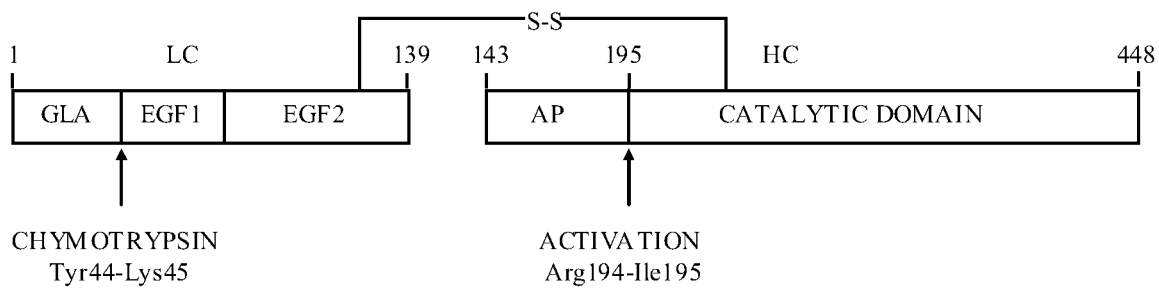

FIG. 3

ANTIDOTES TO FACTOR XA INHIBITORS

CROSS REFERENCE TO RELATED APPLICATIONS

This application is a U.S. National Stage Application under 35 U.S.C. § 371 of International Application No. PCT/US2019/037726, filed on Jun. 18, 2019, which claims the benefit under 35 U.S.C. § 119 (e) of the U.S. Provisional Application Ser. No. 62/686,968, filed Jun. 19, 2018, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Dec. 18, 2020, is named 37JE-257650-US_ST25.txt and is 61,440 bytes in size.

FIELD

The present disclosure relates to the use of factor Xa (fXa) derivatives having reduced or lacking intrinsic procoagulant activity but are also capable of binding and/or neutralizing fXa inhibitors thereby acting as antidotes to anticoagulants targeting fXa.

BACKGROUND

Anticoagulants serve a need in the marketplace in treatment or prevention of undesired thrombosis in patients with a tendency to form blood clots, such as, for example, those patients having clotting disorders, confined to periods of immobility or undergoing medical surgeries. One of the major limitations of anticoagulant therapy, however, is the bleeding risk associated with the treatments, and limitations on the ability to rapidly reverse the anticoagulant activity in case of overdosing or if an urgent surgical procedure is required. Thus, specific and effective antidotes to all forms of anticoagulant therapy are highly desirable. For safety considerations, it is also advantageous to have an anticoagulant-antidote pair in the development of new anticoagulant drugs.

Thus, there is a need for improved antidote agents that do not cause undesired thrombosis and that are effective in substantially neutralizing the anticoagulant activity of a fXa inhibitor in the event of an overdose of the fXa inhibitor or in the event that normal hemostasis needs to be restored to prevent or stop bleeding.

Any and all publications, patents, patent applications mentioned herein are hereby incorporated by reference in their entirety.

SUMMARY

The present disclosure provides modifications to a derivative of the factor Xa (fXa) protein (SEQ ID NO. 13, also referred to as the "r-Antidote"). Compared to the wild-type fXa protein, the r-Antidote has modifications to the Gla domain and the active site, retains fXa's ability to bind to a fXa inhibitor but does not assemble into a prothrombinase complex. Therefore, the r-Antidote can serve as an antidote to fXa inhibitors. The further modifications to the r-Antidote are contemplated to stabilize the antidote and improve its binding efficiency and/or specificity to fXa inhibitors.

One embodiment of the present disclosure provides an isolated two-chain polypeptide comprising an amino acid sequence having at least 80% (or at least 85%, 90% or 95%) sequence identity to SEQ ID NO. 13. This amino acid sequence, in one aspect, (a) is capable of binding to a factor Xa inhibitor and (b) does not assemble into a prothrombinase complex. Further, the amino acid sequence comprises at least one mutation, as compared to SEQ ID NO. 13, selected from (i) a substitution at a D or N residue, (ii) a substitution at a residue in a serine protease specificity pocket, or (iii) a substitution at A290, H147, or D193, wherein the substitution at A290 is not A290S, or combinations thereof.

In one embodiment, the mutation is substitution at one or more D or N residues. In one aspect, the substituted residue is not capable of post-translational deamidation or isoaspartate formation. In one aspect, the substitution is at D12, D29, N59, N71, N86, D114, N163, or N259, or combinations thereof. Non-limiting examples of such substitutions include D12E, D29E, N59Q, N71Q, N71S, N71A, N86Q, N86S, D114E, D114S, N163S, N163Q, N259Q, N259S, and N259A, and combinations thereof.

In some aspects, the substitution is at N86 or D114, or the combination thereof. Non-limiting examples of such substitutions include N86Q, N86S, D114E, and D114S, and combinations thereof.

In one embodiment, the mutation is substitution substitution at a residue in a serine protease specificity pocket. In some aspects, the substitution increases binding affinity to a factor Xa inhibitor relative to a SEQ ID NO. 13. In some aspects, the substitution prevents the polypeptide from binding to a tissue factor pathway inhibitor (TFPI).

In some aspects, the substitution is at V232, V253, D284, A285, V308, G311, A315, G321, or Y323, or combinations thereof. In some aspects, the substitution is at V232, D284, V308, or G311, or combinations thereof. In some aspects, the substitution is selected from the group consisting of V232I, D284M, D284Q, D284S, V308S, G311H, G311K, G311N, G311Q, and G311S, and combinations thereof.

In some aspects, the substitution is selected from a single or a group of substitutions such as D284M; D284M and G311S; D284M, V232I, and V308S; D284M, G311S, V232I, and V308S; D284Q; D284Q and G311S; D284Q, V232I, and V308S; D284Q, G311S, V232I, and V308S; D284S and G311Q; D284S, G311Q, V232I, and V308S; G311K; G311Q; G311N; G311S; G311H; G311K, V232I, and V308S; G311Q, V232I, and V308S; G311N, V232I, and V308S; G311S, V232I, and V308S; G311H, V232I, and V308S; and combinations thereof.

In one embodiment, the mutation comprises a substitution at A290, H147, or D193, wherein the substitution at A290 is not A290S. In one aspect, the substitution is selected from the group consisting of A290N, A290Q, A290K, H147S, H147T, H147N, H147Q, and D193N and combinations thereof.

In some aspects, the substitution is selected from a single or a group of substitutions such as A290N; A290Q; A290K; H147S; H147T; H147N; H147Q; H147S and D193N; H147T and D193N; H147N and D193N; or combinations thereof.

In one embodiment, the antidote polypeptide comprises a mutation to reduce the number of hydrophobic residues at the N-terminus of SEQ ID NO. 13.

Also provided, in one embodiment, is a method of preventing or reducing bleeding in a subject undergoing anticoagulant therapy with a factor Xa inhibitor, comprising administering to the subject an effective amount of the polypeptide of the present disclosure. Further provided is a method of selectively binding and inhibiting an exogenously administered factor Xa inhibitor in a subject undergoing anticoagulant therapy with a factor Xa inhibitor comprising administering to the subject an effective amount of the polypeptide of the present disclosure.

In one aspect of the methods, the factor Xa inhibitor is selected from the group consisting of fondaparinux, idraparinux, biotinylated idraparinux, enoxaparin, dalteparin, NAP-5, rNAPc2, DX-9065a, YM-60828, YM-150, apixaban, rivaroxaban, PD-348292, otamixaban, edoxaban, LY517717, GSK913893, razaxaban, low molecular weight heparin, betrixaban or a pharmaceutically acceptable salt thereof, and combinations thereof. The factor Xa inhibitor ican also be selected from betrixaban, rivaroxaban, apixaban, low molecular weight heparin, and combinations thereof.

In some aspects, the polypeptide is administered prior to a surgery. In some aspects, the subject is a human.

BRIEF DESCRIPTION OF THE DRAWINGS

FIG. 1 shows schematically the domain structure of human factor X (SEQ ID NO. 1) shown in Table 1 as reported in Leytus et al, *Biochem.*, 1986,w 25, 5098-5102. SEQ ID NO. 1 is the amino acid sequence of human fX coded by the nucleotide sequence of human fX (SEQ ID NO. 2) as shown in Table 2 known in the prior art. For example, the translated amino acid sequence is reported in Leytus et al, *Biochem.*, 1986, 25, 5098-5102 and can be found in GenBank, "NM_000504" at <www.ncbi.nlm.nih-.gov/entrez/viewer.fcgi?db=nuccore&id=89142731>. The amino acid numbering in this sequence is based on fX sequence. Human fX precursor (SEQ ID NO. 1) contains a prepro-leader sequence (amino acids 1 to 40 of SEQ ID NO. 1) followed by sequences corresponding to the fX light chain (LC) (amino acids 41 to 179 of SEQ ID NO. 1), the RKR triplet (amino acids 180 to 182 of SEQ ID NO. 1) which is removed during fX secretion, and the fX heavy chain (amino acids 183 to 488 of SEQ ID NO. 1) containing the activation peptide (AP) (amino acids 183 to 234 of SEQ ID NO. 1) and the catalytic domain (amino acids 235 to 488 of SEQ ID NO. 1).

FIG. 2 (SEQ ID NO. 3) shows the amino acid sequence of mature human factor X. The amino acid numbering in this figure is based on mature fX sequence starting from the N-terminal of fX light chain. Factor X circulates in plasma as a two-chain molecule linked by a disulfide bond. The light chain (LC) has 139 amino acid (amino acids 41 through 179 of SEQ ID NO. 1) residues and contains the γ-carboxyglutamic acid (Gla)-rich domain (amino acids 1-45 of SEQ ID NO. 3), including a short aromatic stack (AS) (amino acids 40-45 of SEQ ID NO. 3), followed by two epidermal growth factor (EGF)-like domains (EGF1: amino acids 46-84, EGF2: amino acids 85-128 of SEQ ID NO. 3). The heavy chain (HC) has 306 amino acids and contains a 52 amino acids activation peptide (AP: amino acids 143-194 of SEQ ID NO. 3) followed by the catalytic domain (amino acids 195-448 of SEQ ID NO. 3). The catalytic triad equivalents to H57-D102-S195 in chymotrypsin numbering are located at His236, Asp282, and Ser379 in fX sequence and are underlined (amino acids 236, 282 and 379 of SEQ ID NO. 3).

FIG. 3 shows schematically the domain structure of mature human factor X shown in FIG. 2. The amino acid numbering in this figure is based on mature fX sequence. The cleavage sites for chymotrypsin digestion to remove the Gla-domain containing fragment (amino acid 1-44 of SEQ ID NO. 3) and fX activation to remove the activation peptide are highlighted. Chymotrypic digestion of fXa results in a Gla-domainless fXa lacking the 1-44 amino acid residues (SEQ ID NO. 4).

DETAILED DESCRIPTION

I. Definitions

Figure 4:
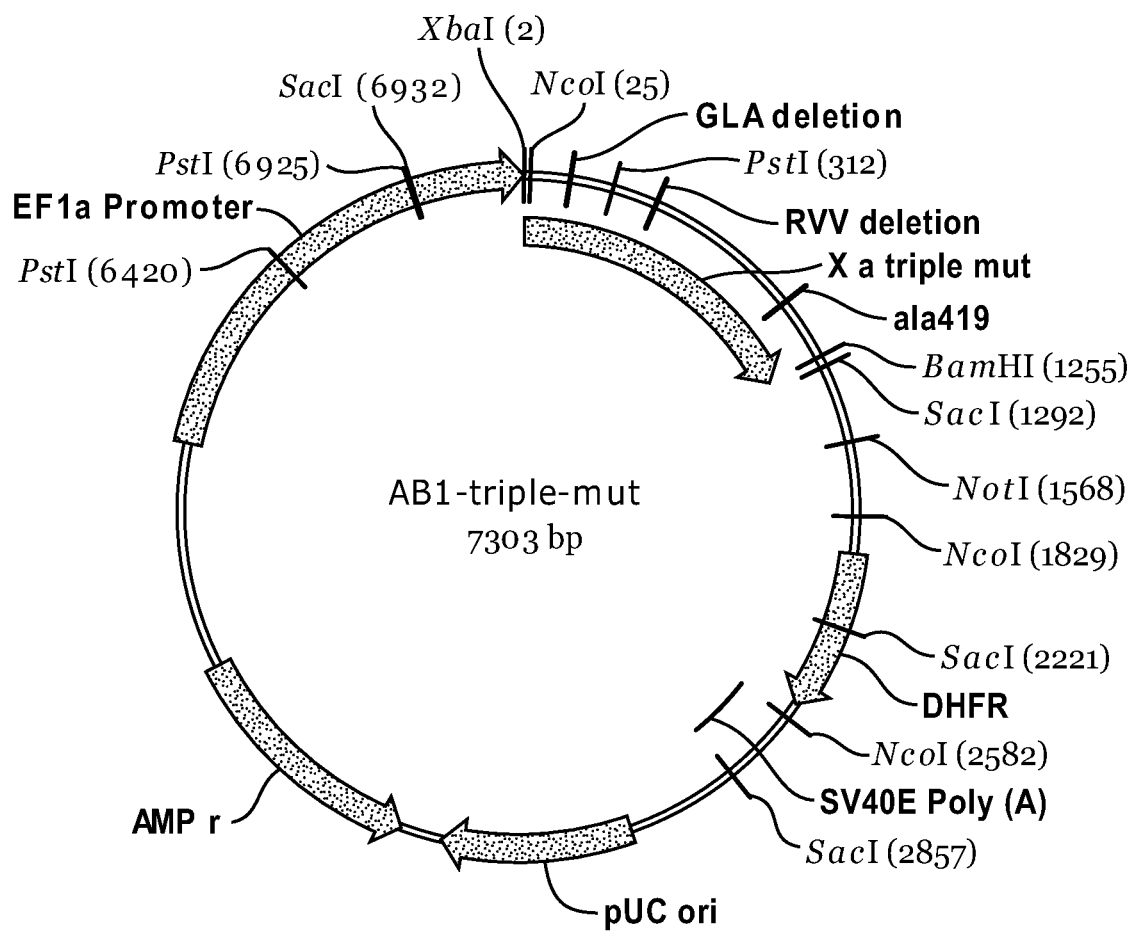
FIG. 4 shows the map of the DNA construct for expression of the fXa triple mutant (SEQ ID NO. 12) in CHO cells. Plasmid DNA was linearized and transfected into CHO dhfr(-) cells. Cells were selected using tetrahydrofolate (HT) deficient media plus methotrexate (MTX). Stable clones were screened for high protein expression by ELISA. The fXa triple mutant was produced in serum free medium and purified by combination of ion exchange and affinity columns. The numbering in the map was based on polynucleotide sequence encoding human fX SEQ ID NO. 1.

All numerical designations, e.g., pH, temperature, time, concentration, and molecular weight, including ranges, are approximations which are varied (+) or (-) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this disclosure. Embodiments defined by each of these transition terms are within the scope of this disclosure.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below. A peptide of three or more amino acids is commonly called an oligopeptide if the peptide chain is short. If the peptide chain is long, the peptide is commonly called a polypeptide or a protein.

| 1-Letter | 3-Letter | Amino Acid |
|---|---|---|
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

"Factor Xa" or "fXa" or "fXa protein" refers to a serine protease in the blood coagulation pathway, which is produced from the inactive factor X (fX). Factor Xa is activated by either factor IXa with its cofactor, factor VIIIa, in a complex known as intrinsic Xase, or factor VIIa with its cofactor, tissue factor, in a complex known as extrinsic Xase. fXa forms a membrane-bound prothrombinase complex with factor Va and is the active component in the prothrombinase complex that catalyzes the conversion of prothrombin to thrombin. Thrombin is the enzyme that catalyzes the conversion of fibrinogen to fibrin, which ultimately leads to blood clot formation. Thus, the biological activity of fXa is sometimes referred to as "procoagulant activity" herein.

The nucleotide sequence coding human factor X ("fX") can be found in GenBank, "NM_000504" at <www.ncbi.nlm.nih.gov/entrez/viewer.fcgi?db=nuccore&id=89142731>, and is listed in FIG. 1b and SEQ ID No. 2. The corresponding amino acid sequence and domain structure of fX are described in Leytus et al, *Biochemistry*, 1986, 25:5098-5102. The domain structure of mature fX is also described in Venkateswarlu, D. et al, *Biophysical Journal,* 2002, 82:1190-1206. Upon catalytic cleavage of the first 52 residues (amino acids 143 to 194 of SEQ ID NO. 3) of the heavy chain, fX is activated to fXa (SEQ ID NO. 6). FXa contains a light chain (SEQ ID NO. 8) and a heavy chain (SEQ ID NO. 9). The first 45 amino acid residues (residues 1-45 of SEQ ID NO. 6) of the light chain is called the Gla domain because it contains 11 post-translationally modified γ-carboxyglutamic acid residues (Gla). It also contains a short (6 amino acid residues) aromatic stack sequence (residues 40-45 of SEQ ID NO. 6). Chymotrypsin digestion selectively removes the 1-44 residues resulting Gla-domainless fXa (SEQ ID NO. 4). The serine protease catalytic domain of fXa locates at the C-terminal heavy chain. The heavy chain of fXa is highly homologous to other serine proteases such as thrombin, trypsin, and activated protein C.

The domain structure of mature factor X may be found in Venkateswarlu D. et al, *Biophysical J.,* 2002, 82, 1190-1206, which is hereby incorporated by reference in its entirety. The amino acid numbering in this figure is the same as in FIG. 3. The tripeptide of Arg140-Lys141-Arg142 (the RKR triplet as shown in FIG. 1) that connects the light chain to the activation peptide is not shown because the form that lacks the tripeptide is predominant in circulation blood plasma. Individual domains are shown in boxes. This includes amino acids 1-45 in FIG. 2 (SEQ ID NO. 3). Functionally important catalytic residues are circled, and "γ" represents Gla (γ-carboxyglutamic acid) residue.

"Native fXa" or "wild-type fXa" refers to the fXa naturally present in plasma or being isolated in its original, unmodified form, which processes the biological activity of activating prothrombin therefore promoting formation of blood clot. The term includes naturally occurring polypeptides isolated from tissue samples as well as recombinantly produced fXa. "Active fXa" refers to fXa having the biological activity of activating prothrombin. "Active fXa" may be a native fXa or modified fXa that retains procoagulant activity.

"fXa Derivatives" or "modified fXa" or "derivatives of a factor Xa protein" refers to fXa proteins that have been modified such that they bind, either directly or indirectly, to a factor Xa inhibitor and do not assemble into the prothrombinase complex. Structurally, the derivatives are modified to provide either no procoagulant activity or reduced procoagulant activity. "Procoagulant activity" is referred to herein as an agent's ability to cause blood coagulation or clot formation. Reduced procoagulant activity means that the procoagulant activity has been reduced by at least about 50%, or more than about 90%, or more than about 95% as compared to wild-type fXa. For example, recombinant fX-S395A essentially has no procoagulant activity as measured by in vitro assays, such as fXa activity assays.

The derivatives have modified active sites, modified Gla domains, and N-terminus. Additional modifications are also contemplated. It is contemplated that such modifications may be made in one or more of the following ways: deletion of one or more of the amino acid from the sequence, substitution of one or more amino acid residues with one or more different amino acid residues, and/or manipulation of one or more amino acid side chains or its "C" or "N" terminals.

The term "active site" refers to the part of an enzyme or antibody where a chemical reaction occurs. A "modified active site" is an active site that has been modified structurally to provide the active site with increased or decreased chemical reactivity or specificity. Examples of active sites include, but are not limited to, the catalytic domain of human factor X comprising the 235-488 amino acid residues (FIG. 1), and the catalytic domain of human factor Xa comprising the 195-448 amino acid residues (FIGS. 2 and 3). Examples of modified active site include, but are not limited to, the catalytic domain of human factor Xa comprising 195-448 amino acid residues in SEQ ID NOS. 11, 12, 13, or 15 with an amino acid substitution at position Ser 379.

As stated above, the derivatives of the disclosure may have modified Gla domains or have the entire Gla domain removed. Examples of fXa derivatives suitable as antidotes in the methods of this disclosure are Gla-domainless fXa (SEQ ID NOS. 4 or 5), Gla-deficient fXa (SEQ ID NO. 7 with modifications described herein), fXa with modifications at the catalytic site (SEQ ID NOS. 10 or 11), and fXa with modifications at the sites known to be important for fV/fVa interaction or fVIII/fVIIIa interaction (SEQ ID NOS. 4, 5, 7, 10, or 11 with at least one amino acid substitution at position Arg306, Glu310, Arg347, Lys351, Lys414 or Arg424), as described in detail herein. Further examples of the fXa derivatives contemplated by this disclosure are provided below.

"Gla-domainless fXa" or "des-Gla fXa" refers to fXa that does not have a Gla-domain and encompasses fXa derivatives bearing other modification(s) in addition to the removal of the Gla-domain. Examples of Gla-domainless fXa in this disclosure include, but are not limited to, fXa derivative lacking the 1-39 amino acid residues of SEQ ID NO. 3; fXa derivative lacking the 6-39 amino acid residues (SEQ ID NO. 16) of SEQ ID NO. 3, corresponding to a fXa mutant expressed in CHO cells described in more details below (SEQ ID NO. 12, Table 12); fXa derivative lacking the 1-44 amino acid residues of SEQ ID NO. 3, corresponding to des-Gla fXa after chymotryptic digestion of human fXa (SEQ ID NO. 4, FIG. 3); and fXa derivative lacking the entire 1-45 Gla-domain residues of SEQ ID NO. 3 as described in Padmanabhan et al, *Journal Mol. Biol.*, 1993, 232:947-966 (SEQ ID NO 5). Other examples include des-Gla anhydro fXa (SEQ ID NO. 10, Table 10) and des-Gla fXa-S379A (SEQ ID NO. 11, Table 11).

In some embodiments, the des-Gla fXa comprises at least amino acid residues 40 to 448 of SEQ ID NO. 3 or an equivalent thereof. In some embodiment, the des-Gla fXa comprises at least amino acid residues 45 to 488 (SEQ ID NO. 4) or 46 to 488 (SEQ ID NO. 5) of SEQ ID NO. 3 or equivalents thereof.

In some embodiment, the des-Gla fXa comprises at least amino acid residues 40 to 139 and 195 to 448 of SEQ ID NO. 3 or equivalents thereof. In some embodiment, the des-Gla fXa comprises at least amino acid residues 45 to 139 and 195 to 448 of SEQ ID NO. 3 or equivalents thereof. In another embodiment, the des-Gla fXa comprises at least amino acid residues 46 to 139 and 195 to 448 of SEQ ID NO. 3 or equivalents thereof.

"Gla-deficient fXa" refers to fXa with reduced number of free side chain γ-carboxyl groups in its Gla-domain. Like Gla-domainless fXa, Gla-deficient fXa can also bear other modifications. Gla-deficient fXa includes uncarboxylated, undercarboxylated and decarboxylated fXa. "Uncarboxylated fXa" or "decarboxylated fXa" refers to fXa derivatives that do not have the γ-carboxy groups of the γ-carboxyglutamic acid residues of the Gla domain, such as fXa having all of its Gla domain γ-carboxyglutamic acid replaced by different amino acids, or fXa having all of its side chain γ-carboxyl removed or masked by means such as amination, esterification, etc. For recombinantly expressed protein, uncarboxylated fXa is, sometimes, also called non-carboxylated fXa. "Undercarboxylated fXa" refers to fXa derivatives having reduced number of γ-carboxy groups in the Gla domain as compared with wild-type fXa, such as fXa having one or more but not all of its Gla domain γ-carboxyglutamic acids replaced by one or more different amino acids, or fXa having at least one but not all of its side chain γ-carboxyl removed or masked by means such as amination and esterification, etc.

The domain structure of human Gla-domainless factor Xa may be found in Padmanabhan et al., *J. Mol. Biol.*, 1993, 232, 947-966, which is hereby incorporated by reference in its entirety. The numbering of the amino acid is based on topological equivalences with chymotrypsin, where, for example, Ser195 corresponds to Ser379 in FIG. 2 when the human mature fX numbering is used. Insertions are indicated with letters, and deletions are indicated by 2 successive numberings. 300 are added to light chain numbering to differentiate from the heavy chain numbering. β363 is β-hydroxy aspartate. Slashes indicate proteolytic cleavages observed in crystalline material. The sequence of Gla-domainless fXa lacking the 1-45 amino acid residues based mature fX (SEQ ID NO. 3) is listed in SEQ ID NO. 5.

In one embodiment, the fXa derivative may lack a light chain of fXa but still contains a serine protease catalytic domain present in the heavy chain. In addition chimeras with other serine protease catalytic domain may be used to make substitutions in the heavy chain.

"pd-Antidote" or "plasma-derived antidote" refers to the des-Gla anhydro fXa derivative and has the amino acid residues of SEQ ID NO. 10.

"r-Antidote" or "recombinant antidote" refers to a fXa derivative lacking the 6-39 amino acid residues of SEQ ID NO. 3, corresponding to a fXa mutant expressed in CHO cells described in more details below (SEQ ID NO. 13, Table 13a-b). The r-Antidote is a two-chain polypeptide, including a light chain and a heavy chain.

"Anticoagulant agents" or "anticoagulants" are agents that inhibit blood clot formation. Examples of anticoagulant agents include, but are not limited to, specific inhibitors of thrombin, factor IXa, factor Xa, factor XIa, factor XIIa or factor VIIa, heparin and derivatives, vitamin K antagonists, and anti-tissue factor antibodies. Examples of specific inhibitors of thrombin include hirudin, bivalirudin (Angiomax®), argatroban and lepirudin (Refludan®). Examples of heparin and derivatives include unfractionated heparin (UFH), low molecular weight heparin (LMWH), such as enoxaparin (Lovenox®), dalteparin (Fragmin®), and danaparoid (Organan®); and synthetic pentasaccharide, such as fondaparinux (Arixtra®). Examples of vitamin K antagonists include warfarin (Coumadin®), phenocoumarol, acenocoumarol (Sintrom®), clorindione, dicumarol, diphenadione, ethyl biscoumacetate, phenprocoumon, phenindione, and tioclomarol. In one embodiment, the anticoagulant is an inhibitor of factor Xa. In one embodiment, the anticoagulant is betrixaban.

"Anticoagulant therapy" refers to a therapeutic regime that is administered to a patient to prevent undesired blood clots or thrombosis. An anticoagulant therapy comprises administering one or a combination of two or more anticoagulant agents or other agents at a dosage and schedule suitable for treating or preventing the undesired blood clots or thrombosis in the patient.

The term "factor Xa inhibitors" or "inhibitors of factor Xa" refer to compounds that can inhibit, either directly or indirectly, the coagulation factor Xa's activity of catalyzing conversion of prothrombin to thrombin in vitro and/or in vivo.

"Direct factor Xa inhibitors" bind to the fXa directly and non-limiting examples include NAP-5, rNAPc2, tissue factor pathway inhibitor, DX-DX-9065a (as described in, e.g., Herbert, J. M., et al, *J Pharmacol Exp Ther.* 1996 276(3): 1030-8), YM-60828 (as described in, e.g., Taniuchi, Y., et al, *Thromb Haemost.* 1998 79(3):543-8), YM-150 (as described in, e.g., Eriksson, B. I. et. al, *Blood* 2005; 106(11), Abstract 1865), apixaban, rivaroxaban, TAK-442, PD-348292 (as described in, e.g., Pipeline Insight: Antithrombotics—Reaching the Untreated Prophylaxis Market, 2007), otamixaban, edoxaban (as described in, e.g., Hylek E M, Curr Opin Invest Drugs 2007 8(9):778-783), LY517717 (as described in, e.g., Agnelli, G., et al, *J. Thromb. Haemost.* 2007 5(4):746-53), GSK913893, razaxaban, betrixaban or a pharmaceutically acceptable salt thereof, and combinations thereof. In a particular aspect, the direct factor Xa inhibitor is rivaroxaban. In some aspects, a direct fXa inhibitor is a small molecule chemical compound.

"Indirect factor Xa inhibitors'" inhibition of the fXa activity is mediated by one or more other factors. Non-limiting examples of indirect factor Xa inhibitors include fondaparinux, idraparinux, biotinylated idraparinux, enoxaparin, fragmin, tinzaparin, low molecular weight heparin ("LMWH"), and combinations thereof. In a particular aspect, the indirect factor Xa inhibitor is enoxaparin.

In one embodiment, the factor Xa inhibitor is selected from betrixaban, rivaroxaban, LMWH, DX-9065a, YM-60828, YM-150, PD-348292, otamixaban, edoxaban, LY517717, GSK913893, razaxaban, apixaban, and combinations thereof.

The term "betrixaban" refers to the compound "[2-({4-[(dimethylamino)iminomethyl]phenyl}carbonylamino)-5-methoxyphenyl]-N-(5-chloro(2-pyridyl))carboxamide" or pharmaceutically acceptable salts thereof. "[2-({4-[(dimethylamino)iminomethyl]phenyl}carbonylamino)-5-methoxyphenyl]-N-(5-chloro(2-pyridyl))carboxamide" refers to the compound having the following structure:

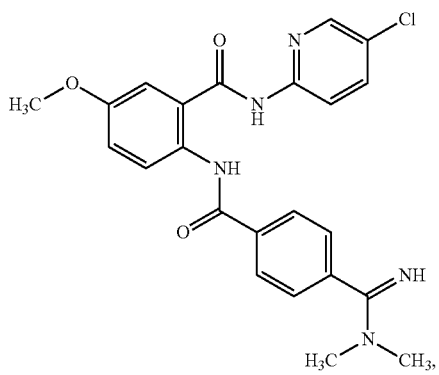 [SMILES: COc1ccc(NC(=O)c2ccc(C(=N)N(C)C)cc2)c(C(=O)Nc2ccc(Cl)cn2)c1]

or a tautomer or pharmaceutically acceptable salt thereof.

Betrixaban is described in U.S. Pat. Nos. 6,376,515 and 6,835,739 and U.S. Patent Application Publication No. 2007/0112039, filed on Nov. 7, 2006, the contents of which are incorporated herein by reference. Betrixaban is known to be a specific inhibitor of factor Xa.

As used herein, the term "antidote" or "antidote to a factor Xa inhibitor" refers to molecules, such as derivatives of fXa, which can substantially neutralize or reverse the coagulation inhibitory activity of a fXa inhibitor by competing with active fXa to bind with available fXa inhibitors. Examples of the antidotes of this disclosure are fXa derivatives with reduced phospholipid membrane binding, such as des-Gla fXa or Gla-deficient fXa, and fXa derivatives with reduced catalytic activity, such as the active site modified fXa derivatives, and derivatives with reduced interaction with fV/Va, or fVIII/fVIIIa. Examples of antidotes of the disclosure with reduced membrane binding and reduced catalytic activity include, but are not limited to, des-Gla anhydro-fXa by chymotryptic digestion of anhydro-fXa (as described in Example 1); des-Gla fXa-S379A (S195A in chymotrypsin numbering) by mutagenesis (as described in Example 6). The antidotes comprise additional mutations as describe throughout. For example, antidotes of this disclosure have mutations wherein the fXa derivatives are capable of binding to a factor Xa inhibitor, do not assemble into a prothrombinase complex, and have at least one mutation selected from preventing post-translational deamidation or isoaspartate formation, increasing binding affinity to small molecule inhibitors of factor Xa, preventing TFPI binding, reducing the number of hydrophobic residues at the N-terminus, or combinations thereof. In addition, antidotes of this disclosure, for example, have mutation to prevent post-translation deamindation or isoaspartate formation. Another example of antidotes of this disclosure have mutation to prevent post-translational methionine oxidation.

Other examples of antidotes of the disclosure include proteins or polypeptides containing serine protease catalytic domains which possess sufficient structural similarity to fXa catalytic domain and are therefore capable of binding direct fXa inhibitors. Examples include, but are not limited to, thrombin which binds to the fXa inhibitor GSK913893 (Young R., et al., Bioorg. Med. Chem. Lett. 2007, 17(10): 2927-2930); plasma kallikrein which binds to the fXa inhibitor apixaban (Luettgen J., et al., Blood, 2006, 108(11) abstract 4130); and trypsin (or its bacterial homolog subtilisin) which binds the fXa inhibitor C921-78 with subnanomolar affinity (Kd=500 pM) (Betz A, et al, Biochem., 1999, 38(44):14582-14591).

In one embodiment, the derivative of the disclosure binds, either directly or indirectly to a factor Xa inhibitor. The terms "binding," "binds," "recognition," or "recognize" as used herein are meant to include interactions between molecules that may be detected using, for example, a hybridization assay. The terms are also meant to include "binding" interactions between molecules. Interactions may be, for example, protein-protein, protein-nucleic acid, protein-small molecule or small molecule-nucleic acid in nature. Binding may be "direct" or "indirect". "Direct" binding comprises direct physical contact between molecules. "Indirect" binding between molecules comprises the molecules having direct physical contact with one or more intermediate molecules simultaneously. For example, it is contemplated that derivatives of the disclosure indirectly bind and substantially neutralize low molecular weight heparin and other indirect inhibitors of factor Xa. This binding can result in the formation of a "complex" comprising the interacting molecules. A "complex" refers to the binding of two or more molecules held together by covalent or non-covalent bonds, interactions or forces.

"Neutralize," "reverse" or "counteract" the activity of an inhibitor of fXa or similar phrases refer to inhibit or block the factor Xa inhibitory or anticoagulant function of a fXa inhibitor. Such phrases refer to partial inhibition or blocking of the function, as well as to inhibiting or blocking most or all of fXa inhibitor activity, in vitro and/or in vivo.

In certain embodiments, the factor Xa inhibitor is neutralized substantially meaning that its ability to inhibit factor Xa, either directly or indirectly, is reduced by at least about 5%, 10%, 15%, 20%, 25%, 30%, 35%, 40%, 45%, 50%, 55%, 60%, 65%, 70%, 75%, 80%, 85%, 90%, 95%, or 100%.

The term "phospholipid membrane binding" refers to an active fXa's ability to bind to the negatively charged phospholipid membrane or other cellular membrane, such as platelets, in the presence of $Ca^{2+}$ ions. This binding is mediated by the γ-carboxyglutamic acid residues in the Gla domain of fXa.

The term "reduced interaction" refers to fXa derivative's diminished ability to bind or form a complex with ions or other co-factors which normally binds or complexes with wild fXa. Examples of such interaction include but are not limited to fXa's binding with $Ca^{2+}$ ions and phospholipid membrane, interaction with fV/fVa, or fVIII/f/VIIIa, etc. It is preferred that the interaction of a fXa derivative with the ions or other co-factors is reduced to 50% of that of a wild fXa. More preferably, the interaction is reduced to 10%, 1%, and 0.1% of that of a wild-type fXa. This refers to the derivatives' ability to "assemble into the prothrombinase complex."

"fXa inhibitor binding activity" refers to a molecule's ability to bind an inhibitor of fXa. An antidote of the present disclosure possesses fXa inhibitor binding activity, whether it is directly or indirectly.

The term "circulating half life" or "plasma half life" refers to the time required for the plasma concentration of an antidote that circulates in the plasma to reduce to half of its initial concentration after a single administration.

The term "conjugated moiety" refers to a moiety that can be added to a fXa derivative by forming a covalent bond with a residue of the fXa derivative. The moiety may bond directly to a residue of the fXa derivative or may form a covalent bond with a linker which in turn forms a covalent bond with a residue of the fXa derivative.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The antibodies can be polyclonal or monoclonal and can be isolated from any suitable biological source, e.g., murine, rat, sheep and canine.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

"An effective amount" refers to the amount of derivative sufficient to induce a desired biological and/or therapeutic result. That result can be alleviation of the signs, symptoms, or causes of a disease, or any other desired alteration of a biological system. In the present disclosure, the result will typically involve one or more of the following: neutralization of a fXa inhibitor that has been administered to a patient, reversal of the anticoagulant activity of the fXa inhibitor, removal of the fXa inhibitor from the plasma, restoration of hemostasis, and reduction or cessation of bleeding. The effective amount will vary depending upon the specific antidote agent used, the specific fXa inhibitor the subject has been administered, the dosing regimen of the fXa inhibitor, timing of administration of the antidote, the subject and disease condition being treated, the weight and age of the subject, the severity of the disease condition, the manner of administration and the like, all of which can be determined readily by one of ordinary skill in the art.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

"Treating" also covers any treatment of a disorder in a mammal, and includes: (a) preventing a disorder from occurring in a subject that may be predisposed to a disorder, but may have not yet been diagnosed as having it, e.g., prevent bleeding in a patient with anticoagulant overdose; (b) inhibiting a disorder, i.e., arresting its development, e.g., inhibiting bleeding; or (c) relieving or ameliorating the disorder, e.g., reducing bleeding.

As used herein, to "treat" further includes systemic amelioration of the symptoms associated with the pathology and/or a delay in onset of symptoms. Clinical and subclinical evidence of "treatment" will vary with the pathology, the individual and the treatment.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. A "subject" of diagnosis or treatment is a cell or a mammal, including a human. Non-human animals subject to diagnosis or treatment include, for example, murine, such as rats, mice, canine, such as dogs, leporids, such as rabbits, livestock, sport animals, and pets.

The agents and compositions of the present disclosure can be used in the manufacture of medicaments and for the treatment of humans and other animals by administration in accordance with conventional procedures, such as an active ingredient in pharmaceutical compositions.

An agent of the present disclosure can be administered for therapy by any suitable route, specifically by parental (including subcutaneous, intramuscular, intravenous and intradermal) administration. It will also be appreciated that the preferred route will vary with the condition and age of the recipient, and the disease being treated.

One can determine if the method, i.e., inhibition or reversal of a factor Xa inhibitor is achieved, by a number of in vitro assays, such as anti-fXa activity assay, thrombin generation assay, and clinical clotting assays such as aPTT, PT and ACT.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

As used herein, the term "equivalent thereof" when referring to a reference protein, polypeptide or nucleic acid, intends those having minimal homology while still maintaining desired functionality. It is contemplated that any modified protein mentioned herein also includes equivalents thereof. For example, the homology can be, at least 75% homology and alternatively, at least 80%, or alternatively at least 85%, or alternatively at least 90%, or alternatively at least 95%, or alternatively 98% percent homology and exhibit substantially equivalent biological activity to the reference polypeptide or protein. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. It should be noted that when only the heavy chain of fXa (or a related serine protease) is used, the overall homology might be lower than 75%, such as, for example, 65% or 50% however, the desired functionality remains. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: www.ncbi.nlm.nih.govicgi-bin/BLAST.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) *Current Protocols in Molecular Biology*. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: www.ncbi.nlm.nih.gov/blast/Blast.cgi, last accessed on Nov. 26, 2007. Biologically equivalent polynucleotides are those having the specified percent homology and encoding a polypeptide having the same or similar biological activity.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof.

II. Antidotes

Factor Xa Antidotes that Include Further Modifications to the r-Antidote

It is contemplated that further modifications to the r-Antidote, which is disclosed in, e.g., U.S. Pat. No. 8,153,590, the content of which is incorporated to the present disclosure by reference, can further improve the stability, binding efficiency and/or binding specificity of the r-Antidote. Like the r-Antidote, the modified antidotes can also be two-chain, including a light chain and heavy chain, but can also be a single-chain having a heavy chain only. When the antidote is two-chain polypeptide, the light chain can be linked to the heavy chain through an interchain disulfide bond between residues 172 and 342 (of SEQ ID NO: 1), for instance.

A. Prevention or Reduction of Deamidation, Isoaspartate Formation or Oxidation

The Asn and Asp side chains in the r-Antidote can potentially undergo post-translational deamidation or isoaspartate formation, which can impact its function or complicate the manufacturing process. Likewise, the Met side chains can potentially undergo post-translational oxidation. Selective substitution of these residues to avoid deamidation, isoaspartate formation or oxidation, therefore, can help ameliorate such potential issues.

Asn and Asp residues at the following locations are potential targets for post-translational deamidation or isoaspartate formation: D12, D29, N59, N71, N86, D114, N163, and N259 (all numbering according to the consecutive amino acid number of light chain and heavy chain sequences of SEQ ID NO. 13, as shown in Table 13b). D12 and D29 are in the EGF-like domain 1, N59, N71 and N86 are in the EGF-like domain 2, and D114, N163 and N259 are in the heavy chain.

Among these residues, N86 and D114 are discovered to be most susceptible to post-translational deamidation or isoaspartate formation, and D12, D29 and N59 are also likely targets.

These Asn or Asp can be modified, derivatized or substituted to prevent or reduce deamidation or isoaspartate formation. For instance, they can substituted with E, Q, S, or A. More particularly, non-limiting examples of substitutions include D12E, D29E, N59Q, N71Q, N71S, N71A, N86Q, N86S, D114E, D114S, N163S, N163Q, N259Q, N259S, and N259A.

In some aspects, one or more of the Met residues are substituted with a different residue, such as but not limited to A, S, T, N, Q, D, E, H, K, or R.

B. Modifications to the "Specificity Pocket"

Serine proteases, such as fXa, possess a structurally distinct site (often referred to as the "specificity pocket" or S1 subsite) near the catalytic serine residue that accommodates an amino acid from a peptide/protein substrate. Each serine protease has a unique set of amino acids that form the envelope of the pocket and provide unique structure that can accommodate only specific substrate amino acid side chains (e.g., Arg, Lys for trypsin; Phe for chymotrypsin).

It is contemplated that modification of one or more of the residues in the specificity pocket can help improve the binding affinity or specificity of the r-Antidote. Such modifications can be selected to avoid or minimize their impact on other functions of the antidote.

For instance, crystal structures of serine proteases show that adjacent to the specificity pocket is a system of water channels. These channels allow water molecules in the pocket to exit when the substrate side-chain inserts into the pocket. Crystal structures also show that the water molecules form a system of hydrogen-bonds with each other and with the protease backbone/side-chains that maintains the structural integrity of the protease. Since these water channels are an integral part of the specificity pocket and indeed of the protease structure, it is contemplated that a modification of a residue in the pocket needs to maintain the water channel integrity.

In one aspect, the modification can include one or more substitutions at, as compared to SEQ ID NO: 13 (r-Antidote), V232, V253, D284, A285, V308, G311, A315, G321, or Y323. In particular, the sites V232, D284, V308, and G311 are contemplated to be effective. Without limitation, the substitutions can be V232I, D284M, D284Q, D284S, V308S, G311H, G311K, G311N, G311Q, and G311S.

In some aspects, modeling shows that certain combinations of substitutions can be effective in improving the binding affinity. Non-limiting examples of such combinations of substitutions include,
i) D284M;
ii) D284M and G311S;
iii) D284M, V232I, and V308S;
iv) D284M, G311S, V232I, and V308S;
v) D284Q;
vi) D284Q and G311S;
vii) D284Q, V232I, and V308S;
viii) D284Q, G311S, V232I, and V308S;
ix) D284S and G311Q;
x) D284S, G311Q, V232I, and V308S;
xi) G311K;
xii) G311Q;
xiii) G311N;
xiv) G311S;
xv) G311H;
xvi) G311K, V232I, and V308S;
xvii) G311Q, V232I, and V308S;
xviii) G311N, V232I, and V308S;
xix) G311S, V232I, and V308S;
xx) G311H, V232I, and V308S.

As provided, these substitutions and combinations of substitutions are contemplated to be able to increase binding affinity of the antidote to fXa inhibitors.

The factor Xa inhibitor, in one aspect, is a direct factor Xa inhibitor (e.g., small molecule inhibitors), such as but not limited to NAP-5, rNAPc2, tissue factor pathway inhibitor, DX-9065a, YM-60828, YM-150, apixaban, rivaroxaban, TAK-442, PD-348292, otamixaban, edoxaban, LY517717, GSK913893, razaxaban, betrixaban or a pharmaceutically acceptable salt thereof, and combinations thereof. In a particular aspect, the direct factor Xa inhibitor is rivaroxaban.

The factor Xa inhibitor, in one aspect, is an indirect factor Xa inhibitor, such as but not limited to fondaparinux, idraparinux, biotinylated idraparinux, enoxaparin, fragmin, tinzaparin, low molecular weight heparin and combinations thereof. In a particular aspect, the indirect factor Xa inhibitor is enoxaparin.

In some aspects, the modification is contemplated to be able to prevent the antidote from binding to a tissue factor pathway inhibitor (TFPI).

It is contemplated that amino acids at subsites other than in the specificity pocket can also be altered. Such amino acids include, for instance, T189, Y190, F267, or I268, or combinations thereof (relative to SEQ ID NO. 13). Non-limiting examples of substitutions include T189W, Y190W, F267W, I268W, or combinations thereof. Such substitutions are contemplated to increase hydrophobic interaction of the protein with small molecule inhibitors.

In another aspect, the substitution can be made at amino acids at the following loops surrounding the fXa active site, T186-Y190, R237-R243, S265-I268, or G311-G313.

C. Modifications in the Catalytic Triad

The antidotes of the present disclosure do not have catalytic or have reduced catalytic capabilities. The r-Antidote, for instance, has a Ser195Ala (according to protease numbering, which is at position 290 of SEQ ID NO. 13) substitution at the active site. Further modifications at this position (not to change back to Ser) as well as the other two residues of the catalytic triad (His57 and Asp102 according to chymotrypsin numbering or H147 and D193 as shown in SEQ ID NO. 13), it is contemplated, can further improve the antidote's affinity to fXa inhibitors (direct or indirect) without restoring the protein's catalytic capability.

Example substitutions of A290 can include Asn, Gln, and Lys among others. The Asn could form hydrogen-bonds to H147 and rivaroxaban>C=O. Gln and Lys could add hydrophobic interaction with the small molecules.

Example substitutions of H147 include Ser, Thr, Asn, and Gln among others. Changes at H147 could be in addition to A290 changes; however changes at H147 can also take into consideration their effect on D193 since D193 is buried and interacts directly with H147. If H147 is altered to Ser, Thr, or Asn, D193 could be maintained or altered to Asn.

Therefore, in one aspect, the antidote of the present disclosure include one or more substitutions at one or more of A290, H147, or D193 (of SEQ ID NO. 13).

In some aspects, the substitutions can be A290N, A290Q, A290K, H147S, H147T, H147N, H147Q, or D193N. In some aspects, the substitutions, or combinations of substitutions, include, i) A290N;
ii) A290Q;
iii) A290K;
iv) H147S;
v) H147T;
vi) H147N;
vii) H147Q;
viii) H147S and D193N;
ix) H147T and D193N;
x) H147N and D193N; or combinations thereof.

D. Modifications at N-Terminus or EGF Domains

In one embodiment, the antidote of the present disclosure can include one or more mutations to reduce the number of hydrophobic residues at the N-terminus as compared to the r-Antidote (SEQ ID NO. 13). In this aspect, a polypeptide wherein the mutation is at an amino acid residue between A1-K11 (of SEQ ID NO. 13). In further aspect, the mutation is at an amino acid residue between A1-Y10. In another aspect, the mutation is a deletion of an amino acid residue between A1-Y10 and a substitution of K11 to a G. In still another aspect, the mutation is a deletion of an amino acid residue between A1-Y10 and a substitution of K11 to an A.

In a further embodiment, the antidote is a combination of SEQ ID NO. 13 and SEQ ID NO. 16, wherein SEQ ID NO. 16 has at least one amino acid mutation, substitution or modification and is inserted between L5 and F6 of SEQ ID NO. 13.

In one aspect, the antidote of the present disclosure includes a mutation, as compared to the r-Antidote, to prevent post-translational methionine oxidation. The mutation to prevent post-translation methionine oxidation can include M273I, M273L or M273V.

In one aspect, the N-terminus of antidote can be altered to begin with any of the following amino acid sequences DGD, KDGD, GDGD, ADGD. Such modification would, for example, reduce the number of hydrophobic residues at the N-terminus of the antidote. Alternatively, one or both of the EGF-like domains could be deleted so that the construct would comprise only EGF-like domain 2:heavy chain or only the heavy chain protease domain. In another embodiment, only the serine protease domain is used, for example, alteration of residues in the heavy chain would be required. A substitution C221S or C221A (as compared to SEQ ID NO. 13) would be required, in this embodiment, and changes at the other residues would be in addition to C221 and could be in any combination.

It is contemplated that further truncations at the fXa light chain, for example, additional deletion of the EGF1 domain, EGF1 plus EGF2 domains, or fragments thereof, and inactive fXa with only the heavy chain may be useful antidotes of this disclosure.

E. Combinations of Modifications

Combinations of different types of modifications are also contemplated. In one aspect, the antidote includes (i) substitution of one or more Asn and Asp residues at D12, D29, N59, N71, N86, D114, N163, and N259 and (ii) one or more substitutions at residues in the specificity pocket, e.g., V232, V253, D284, A285, V308, G311, A315, G321, or Y323. In one aspect, the Asn or Asp is selected from N86 or D114, or from D12, D29 or N59. In one aspect, the residues in the specificity pocket is selected from V232, D284, V308, and G311.

In another aspect, the antidote includes (i) substitution of one or more Asn and Asp residues at D12, D29, N59, N71, N86, D114, N163, and N259 and (iii) substitution at one or more residues at the catalytic triad (e.g., A290, H147, or D193). In one aspect, the Asn or Asp is selected from N86 or D114, or from D12, D29 or N59. In one aspect, the residue at the catalytic triad is A290.

In one aspect, the antidote includes one or more of (i) substitution of one or more Asn and Asp residues at D12, D29, N59, N71, N86, D114, N163, and N259, (ii) one or more substitutions at residues in the specificity pocket, e.g., V232, V253, D284, A285, V308, G311, A315, G321, or Y323, or (iii) substitution at one or more residues at the catalytic triad (e.g., A290, H147, or D193), and (iv) a modification at the N-terminus or EGF domains as described above.

Combinations can also include one or more of the above modification and one or more known modifications such as those disclosed in WO/2010/117729, the content of which is incorporated herein by reference. In one aspect, the additional modification is deleting all or part of the activation peptide at the N-terminus of the heavy chain. In one embodiment, this includes deletion of all of part of the activation peptide or amino acid residues 143-194 of SEQ ID NO. 3 or an equivalent thereof.

In another embodiment, the additional modification is an amino acid modification that prevents cleavage of a β-peptide wherein β-peptide refers to a portion of or the entire heavy chain. This modification can include deletion, substitution, or insertion of an amino acid. On such modification includes substitutions of one or more of Arg429 or Ser436 (chymotrypsin numbering). In still another embodiment, the additional modification a deletion of a β-peptide. In one embodiment, the deletion of the β-peptide comprises a deletion of at least amino acid residues 430-448 of SEQ ID NO. 3 or an equivalent thereof.

In one embodiment, the additional modification includes mutations at fXa residues known to be important for fXa interaction with cofactor fV/fVa. Such residues include, without limitation, Arg306, Glu310, Arg347, Lys351, or Lys414 (SEQ ID NOS. 3 and 7, these amino acids correspond to Arg125, Glu129, Arg165, Lys169, Lys230 in the chymotrypsin numbering). In addition, mutations at fXa residues known to be important for fVII/fVIIIa interaction, such as Arg424 in SEQ ID NOS. 3 and 7 (Arg240 in chymotrypsin numbering), may also be used as fXa inhibitor antidotes.

Other modification of active site residues of fXa or residues known to be important for serine protease interactions can also be included such as, for example, replacement of Glu216, Glu218, and Arg332 in SEQ ID NOS. 3 and 7 (Glu37, Glu39, and Arg150 in chymotrypsin numbering, respectively) with other amino acid residues.

Still in further embodiments, the additional modification can be mutations at the autolysis loop of FXa heavy chain to eliminate potential degradation. FXa, like other serine proteases of the family, has an exposed surface loop (autolysis loop) which is susceptible to cleavage by various proteases. This loop, including amino acids 366 to 376 of SEQ ID NO. 1, contains several positively charged residues (Arg366, Lys370, Arg372, Arg376) with Arg372 as the potential recognition site for cleavage. These charged residues can be mutated to Gln (Q) or Ala (A) to prohibit the possible cleavage. In one aspect, the mutation is Arg366Q/A. In another aspect, the mutation is Lys370Q/A. In yet another aspect, the mutation is Arg372Q/A. In yet another aspect, the mutation is Arg376Q/A. In some embodiments, a fXa derivative has one or more such mutations.

III. Methods of Preparing Antidotes

Polypeptides of this disclosure can be prepared by expressing polynucleotides encoding the polypeptide sequences of this disclosure in an appropriate host cell. This can be accomplished by methods of recombinant DNA technology known to those skilled in the art. The proteins and polypeptides of this disclosure also can be obtained by chemical synthesis using a commercially available automated peptide synthesizer such as those manufactured by Perkin Elmer/Applied Biosystems, Inc., Model 430A or 431A, Foster City, CA, USA. The synthesized protein or polypeptide can be precipitated and further purified, for example by high performance liquid chromatography (HPLC). Accordingly, this disclosure also provides a process for chemically synthesizing the proteins of this disclosure by providing the sequence of the protein and reagents, such as amino acids and enzymes and linking together the amino acids in the proper orientation and linear sequence.

It is known to those skilled in the art that modifications can be made to any peptide to provide it with altered properties. Polypeptides of the disclosure can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that α-helical secondary structure or random secondary structure is preferred.

In a further embodiment, subunits of polypeptides that confer useful chemical and structural properties will be chosen. For example, peptides comprising D-amino acids may be resistant to L-amino acid-specific proteases in vivo. Modified compounds with D-amino acids may be synthesized with the amino acids aligned in reverse order to produce the peptides of the disclosure as retro-inverso peptides. In addition, the present disclosure envisions preparing peptides that have better defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2NH$—$R_2$, where $R_1$, and $R_2$ are amino acid residues or sequences. A reduced peptide bond may be introduced as a dipeptide subunit. Such a molecule would be resistant to peptide bond hydrolysis, e.g., protease activity. Such molecules would provide ligands with unique function and activity, such as extended half-lives in vivo due to resistance to metabolic breakdown, or protease activity. Furthermore, it is well known that in certain systems constrained peptides show enhanced functional activity (Hruby (1982) Life Sciences 31:189-199 and Hruby et al. (1990) Biochem J. 268:249-262); the present disclosure provides a method to produce a constrained peptide that incorporates random sequences at all other positions.

The following non-classical amino acids may be incorporated in the peptides of the disclosure in order to introduce particular conformational motifs: 1,2,3,4-tetrahydroisoquinoline-3-carboxylate (Kazrnierski et al. (1991) J. Am. Chem. Soc. 113:2275-2283); (2S,3 S)-methyl-phenylalanine, (2 S,3R)— methyl-phenylalanine, (2R,3S)-methyl-phenylalanine and (2R,3R)-methyl-phenylalanine (Kazmierski and Hruby (1991) Tetrahedron Lett. 32(41):5769-5772); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1989) J. Takeda Res. Labs. 43:53-76) histidine isoquinoline carboxylic acid (Zechel et al. (1991) Int. J. Pep. Protein Res. 38(2):131-138); and HIC (histidine cyclic urea), (Dharanipragada et al. (1993) Int. J. Pep. Protein Res. 42(1):68-77) and (Dharanipragada et al. (1992) Acta. Crystallogr. C. 48:1239-1241).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al. (1985) J. Org. Chem. 50:5834-5838); β-sheet inducing analogs (Kemp et al. (1988) Tetrahedron Lett. 29:5081-5082); β-turn inducing analogs (Kemp et al. (1988) Tetrahedron Lett. 29:5057-5060); α-helix inducing analogs (Kemp et al. (1988) Tetrahedron Lett. 29:4935-4938); α-turn inducing analogs (Kemp et al. (1989) J. Org. Chem. 54:109:115); analogs provided by the following references: Nagai and Sato (1985) Tetrahedron Lett. 26:647-650; and DiMaio et al. (1989) J. Chem. Soc. Perkin Trans. p. 1687; a Gly-Ala turn analog (Kahn et al. (1989) Tetrahedron Lett. 30:2317); amide bond isostere (Clones et al.

(1988) Tetrahedron Lett. 29:3853-3856); tetrazole (Zabrocki et al. (1988) J. Am. Chem. Soc. 110:5875-5880); DTC (Samanen et al. (1990) Int. J. Protein Pep. Res. 35:501:509); and analogs taught in Olson et al. (1990) J. Am. Chem. Sci. 112:323-333 and Garvey et al. (1990) J. Org. Chem. 56:436. Conformationally restricted mimetics of beta turns and beta bulges, and peptides containing them, are described in U.S. Pat. No. 5,440,013, issued Aug. 8, 1995 to Kahn.

It is known to those skilled in the art that modifications can be made to any peptide by substituting one or more amino acids with one or more functionally equivalent amino acids that does not alter the biological function of the peptide. In one aspect, the amino acid that is substituted by an amino acid that possesses similar intrinsic properties including, but not limited to, hydrophobicity, size, or charge. Methods used to determine the appropriate amino acid to be substituted and for which amino acid are known to one of skill in the art. Non-limiting examples include empirical substitution models as described by Dahoff et al. (1978) In Atlas of Protein Sequence and Structure Vol. 5 suppl. 2 (ed. M. O. Dayhoff), pp. 345-352. National Biomedical Research Foundation, Washington DC; PAM matrices including Dayhoff matrices (Dahoff et al. (1978), supra, or JTT matrices as described by Jones et al. (1992) Comput. Appl. Biosci. 8:275-282 and Gonnet et al. (1992) Science 256:1443-1145; the empirical model described by Adach and Hasegawa (1996) J. Mol. Evol. 42:459-468; the block substitution matrices (BLOSUM) as described by Henikoff and Henikoff (1992) Proc. Natl. Acad. Sci. USA 89:10915-10919; Poisson models as described by Nei (1987) Molecular Evolutionary Genetics. Columbia University Press, New York; and the Maximum Likelihood (ML) Method as described by Müller et al. (2002) Mol. Biol. Evol. 19:8-13.

IV. Methods of Using Factor Xa Antidotes

The present disclosure relates to therapeutic methods of preventing or reducing bleeding in a subject undergoing anticoagulant therapy. It is contemplated that the antidotes of the present disclosure may be short-duration drugs to be used in elective or emergency situations which can safely and specifically neutralize a fXa inhibitor's conventional anticoagulant properties without causing deleterious hemodynamic side-effects or exacerbation of the proliferative vascular response to injury.

One aspect of the present disclosure relates to methods for preventing or reducing bleeding in a subject undergoing anticoagulant therapy with a factor Xa inhibitor, by administering to the subject an effective amount of an antidote of the present disclosure.

In another aspect the method provided herein selectively binds and inhibits an exogenously administered factor Xa inhibitor in a subject undergoing anticoagulant therapy with a factor Xa inhibitor comprising administering to the subject an effective amount of an antidote of the present disclosure. The subject may be a cell or a mammal, such as a human.

Patients suitable for this therapy have undergone prior anticoagulant therapy, for example, they have been administered one or more of an anticoagulant, such as an inhibitor of factor Xa.

The factor Xa inhibitor, in one aspect, is a direct factor Xa inhibitor (e.g., small molecule inhibitors), such as but not limited to NAP-5, rNAPc2, tissue factor pathway inhibitor, DX-9065a, YM-60828, YM-150, apixaban, rivaroxaban, TAK-442, PD-348292, otamixaban, edoxaban, LY517717, GSK913893, razaxaban, betrixaban or a pharmaceutically acceptable salt thereof, and combinations thereof. In a particular aspect, the direct factor Xa inhibitor is rivaroxaban.

The factor Xa inhibitor, in one aspect, is an indirect factor Xa inhibitor, such as but not limited to fondaparinux, idraparinux, biotinylated idraparinux, enoxaparin, fragmin, tinzaparin, low molecular weight heparin and combinations thereof. In a particular aspect, the indirect factor Xa inhibitor is enoxaparin.

Also provided by this disclosure are pharmaceutical compositions containing one or more of the antidotes of the present disclosure and a pharmaceutically acceptable carrier. The compositions are administered to a subject in need thereof in an amount that will provide the desired benefit, a reduction or stopping of bleeding. The compositions can be co-administered with any suitable agent or therapy that complements or enhances the activity of the factor Xa antidotes. An example of such is a second agent capable of extending the plasma half-life of the antidote. Examples of suitable second agents include but are not limited to an anti-fXa antibody recognizing the exosite of fXa heavy chain or an alpha-2-macroglobulin bound fXa antidote. Formation of the complex between fXa antidote and a second agent (exosite antibody or alpha-2-macroglobulin) would block macromolecular interactions but retains the ability of active site dependent inhibitor bindings. Examples of anti-fXa antibodies suitable for co-administration include but are not limited to those described in Yang Y. H., et al, *J. Immunol.* 2006, 1; 177(11):8219-25, Wilkens, M and Krishnaswamy, S., *J. Bio. Chem.*, 2002, 277 (11), 9366-9374, and Church W R, et al, *Blood,* 1988, 72(6), 1911-1921.

In some embodiments, the antidote is administered after the administration of an overdose of a fXa inhibitor or prior to a surgery, which may expose subjects to the risk of hemorrhage.

In any of the methods described herein, it should be understood, even if not always explicitly stated, that an effective amount of an antidote of the present disclosure is administered to the subject. The amount can be empirically determined by the treating physician and will vary with the age, gender, weight and health of the subject. Additional factors to be considered by the treating physician include but are not limited to the identity and/or amount of factor Xa inhibitor, which may have been administered, the method or mode that the antidote will be administered to the subject, the formulation of the antidote, and the therapeutic end point for the patient. With these variables in mind, one of skill will administer a therapeutically effective amount to the subject to be treated. It is contemplated that a therapeutically effective amount of the antidotes described herein sufficient to counteract, or substantially neutralize, an anticoagulant in a subject may contain from about 0.01 milligram of antidote per kilogram of a subject's body weight to 1 gram of antidote per kilogram of a subject's body weight of antidote. It is further contemplated that the antidote may be provided to the subject in a concentration a range of from about 10 nanomolar to about 100 micromolar, or about 10 nanomolar to about 5 micromolar, or about 100 nanomolar to about 2.5 micromolar.

Some of the modifications disclosed herein can increase the neutralizing capability of the antidote. Accordingly, the effective dose can be lower, such as from about 0.001 milligram of antidote per kilogram of a subject's body weight to 0.5 gram of antidote per kilogram of a subject's body weight of antidote.

In certain aspects, unit dose formulations are provided that includes from about 1, 2, 3, 4, 5, 6, 7 or 8 milligrams (mg) to about 0.5, 1, or 1.5 grams (g). Other amounts contemplated by this invention include from about 50 mg to about 1 g; from about 100 mg to about 0.8 g; and from about 200 mg to about 500 mg.

In another embodiment, the unit dose formulation is administered in a neutralizing amount that is at least about a 0.5:1 fold molar ratio of circulating concentration of polypeptide over circulating concentration of the factor Xa inhibitor for a period of at least about 30 minutes. In other embodiments the molar ratio is about 0.1:1, or about 0.2:1 or about 1:1.

The formulation when administered neutralizes the factor Xa inhibitor by at least about 20%, or by at least about 50%, or by at least about 75%, or by at least about 90%, or by at least about 95%.

The compositions can be administered in amounts that are effective for the antidote to selectively recognize and bind, either directly or indirectly, the factor Xa inhibitor in the subject. They also can be administered in amounts to substantially inhibit or substantially neutralize exogenously administered factor Xa inhibitors in a subject.

In some embodiments, the antidote is any one of the antidotes as described above. In some embodiments, the antidote is conjugated with a moiety capable of extending the circulating half-life of the antidote. In some embodiments, the moiety is selected from the group consisting of polyethylene glycol, an acyl group, a liposome, a carrier protein, an artificial phospholipid membrane, and a nanoparticle. For example, a non-active site lysine or cysteine residue of a fXa antidote described herein may be chemically modified to attach to a polyethylene glycol molecule. Other methods provided in Werle, M. & Bernkop-Schnürch, A. Strategies to Improve Plasma Half Life Time of Peptide and Protein Drugs, *Amino Acids* 2006, 30(4):351-367 may be used to extend the plasma half-life of the antidotes of this disclosure.

In other embodiments of the disclosure, the half-life of an antidote of the present disclosure is improved by coupling the antidote to Fc carrier domains. In one embodiment, the antidote is coupled to an Fc fragment, such as an immunoglobulin peptide portion or an IgG1 fragment. In one embodiment, a chimeric protein is contemplated which comprises the fXa antidote and the immunoglobulin peptide portion. In yet another embodiment, the fXa antidote and the immunoglobulin peptide is coupled by a chemical reaction, such as a disulfide bond with the human IgG heavy chain and kappa light chain constant regions.

In one embodiment, the therapeutically effective amount of an antidote exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals. The antidotes of this disclosure may be administered once or several times when needed to neutralize the effect of a fXa inhibitor present in a subject's plasma. Preferably, the antidotes of this disclosure is sufficient when administered in a single dose.

It is contemplated that a typical dosage of the antidotes of the disclosure will depend on the actual clinical setting and inhibitor concentration in plasma. In in vitro assay, such as anti-fXa activity assay and thrombin generation, clinical clotting assays such as aPTT, PT and ACT, a therapeutically effective amount of an antidote is expected to produce a correction of ex vivo clotting activity of 10% or more. In vitro assays indicate that an antidote/inhibitor ratio>1.0 should show reversal effect. The maximum plasma concentration for antidote is expected to be in the micro molar range, probably between 10 micromolar or below.

In a clinical setting, one of the criteria in determining the effectiveness of an antidote is that it produces any change of actual measures of bleeding. In clinical trials, categories of major bleeds include fatal hemorrhage, bleeds into vital organs (intracranial, intraocular, retroperitoneal, spinal, pericardial), any bleed requiring re-operation or a new therapeutic procedure (e.g., aspiration of an operated knee, thoracotomy tube insertion for hemothorax, endoscopic electrocoagulation, etc) or a bleeding index of ≥2.0 if it is associated with an overt bleed. The bleeding index is defined as the number of units of packed red cells or whole blood transfused plus the hemoglobin values before the bleeding episode minus the hemoglobin values after the bleed has stabilized (in grams per deciliter).

Another criterion for antidote efficacy in clinical settings is that it reduces clinically significant non-major bleeding. This category of hemorrhages include bleeding that is not major but is more than usual and warrants clinical attention, including epistaxis that is persistent or recurrent and in substantial amount or will not stop without intervention; rectal or urinary tract bleeding that does not rise to a level requiring a therapeutic procedure (e.g., new insertion of a Foley catheter or cystoscopic inspection), substantial hematomas at injection sites or elsewhere that are spontaneous or occur with trivial trauma; substantial blood loss; bleeding requiring unplanned transfusion. As used herein, "substantial blood loss" refers to amount of blood loss that is more than that amount usually associated with surgical procedure. Substantial blood loss leads to swelling that is managed conservatively because it falls short of requiring drainage.

In one embodiment, the antidotes of the present disclosure have sufficient plasma circulating half-life for substantially neutralizing the fXa inhibitor present in plasma. Activated fXa has essentially no circulating half-life in humans, as it is effectively inhibited by ATIII, TFPI and other plasma inhibitors (Fuchs, H. E. and Pizzo, S. V., *J. Clin. Invest.*, 1983, 72:2041-2049). Inactive fXa has been shown to have a circulating half-life of 2-3 hours in humans. In a baboon model, the half-life of a fXa blocked in the active site by DEGR ([5-(dimethylamino) 1-naphthalenesulfonyl]-glutamylglycylarginyl chloromethyl ketone) was approximately 10 hours or 2 hours, as determined by isotopic or enzyme-linked immunosorbent assays, respectively (Taylor, F. B. et al, *Blood*, 1991, 78(2):364-368).

It may be desirable to extend the half life of an antidote to 24-48 hours. It is contemplated that conjugation or addition of one or more of the following moieties will increase the plasma half life of an antidote:
  a) polyethylene glycol;
  b) an acyl group;
  c) liposomes and encapsulating agents;
  d) carrier proteins;
  e) artificial phospholipid membrane;
  f) immunoglobulin; and
  g) nanoparticle.

The conjugation site may not be limited to special chain or residue so long as the conjugation does not mask the inhibitor binding site(s) of the antidote. The antidotes described herein may be administered in combination with any one or more than one of the compounds described above.

In general, administered antibodies have much longer half-life than circulating blood coagulation proteins. It is possible to use a complex consisting of Gla-domain deficient fXa and an antibody bound to the exosite of fXa as an antidote with extended circulating half-life. Formation of a complex between fXa and the antibody targeting the exosite may reduce interaction of an Gla-domain deficient fXa with macromolecular substrates and inhibitors, such as prothrombin and antithrombin III, while leaving the active site cleft unperturbed so that the complex can act as an antidote to bind active site directed direct inhibitor. Formation of $\alpha$-2-macroglobulin-fXa complex can also be of useful as an antidote for fXa direct inhibitors.

Efficacy of the antidotes in reversal of the anticoagulant activity of fXa inhibitors as well as its procoagulant activity may be determined by in vitro assays and animal models by those of skill in the art. Examples of in vitro assays are anti-fXa activity assay, thrombin generation, clinical clotting assays such as aPTT, PT and ACT. An antidote of this disclosure is contemplated to be capable of producing 10% or more correction of ex vivo clotting activity. Several in vivo animal models of bleeding time and/or blood loss in, for example, rodents, such as mice, dogs and primates, such as monkeys, may be used to measure efficacy.

V. Polynucleotides, Host Cells and Compositions

This disclosure also provides polynucleotides the encode any polypeptide of the present disclosure, and their complements. Complementarity can be determined using traditional hybridization under conditions of moderate or high stringency. As used herein, the term polynucleotide intends DNA and RNA as well as modified nucleotides. For example, this disclosure also provides the anti-sense polynucleotide stand, e.g. antisense RNA to these sequences or their complements.

Also provided are polynucleotides encoding substantially homologous and biologically equivalent polypeptides to the inventive polypeptides and polypeptide complexes. Substantially homologous and biologically equivalent intends those having varying degrees of homology, such as at least 65%, or alternatively, at least 70%, or alternatively, at least 75%, or alternatively at least 80%, or alternatively, at least 85%, or alternatively at least 90%, or alternatively, at least 95%, or alternatively at least 97% homologous as defined above and which encode polypeptides having the biological activity to bind factor Xa inhibitors and do not assemble into the prothrombinase complex as described herein. It should be understood although not always explicitly stated that embodiments to substantially homologous polypeptides and polynucleotides are intended for each aspect of this disclosure, e.g., polypeptides, polynucleotides and antibodies.

The polynucleotides of this disclosure can be replicated using conventional recombinant techniques. Alternatively, the polynucleotides can be replicated using PCR technology. PCR is the subject matter of U.S. Pat. Nos. 4,683,195; 4,800,159; 4,754,065; and 4,683,202 and described in PCR: The Polymerase Chain Reaction (Mullis et al. eds, Birkhauser Press, Boston (1994)) and references cited therein. Yet further, one of skill in the art can use the sequences provided herein and a commercial DNA synthesizer to replicate the DNA. Accordingly, this disclosure also provides a process for obtaining the polynucleotides of this disclosure by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can operatively link the polynucleotides to regulatory sequences for their expression in a host cell. The polynucleotides and regulatory sequences are inserted into the host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

RNA can be obtained by first inserting a DNA polynucleotide into a suitable prokaryotic or eukaryotic host cell. The DNA can be inserted by any appropriate method, e.g., by the use of an appropriate gene delivery vehicle (e.g., liposome, plasmid or vector) or by electroporation. When the cell replicates and the DNA is transcribed into RNA; the RNA can then be isolated using methods well known to those of skill in the art, for example, as set forth in Sambrook and Russell (2001) supra. For instance, mRNA can be isolated using various lytic enzymes or chemical solutions according to the procedures set forth in Sambrook and Russell (2001) supra or extracted by nucleic-acid-binding resins following the accompanying instructions provided by manufactures.

This disclosure also provides an antibody capable of specifically forming a complex with a protein or polypeptide of this disclosure, which are useful in the therapeutic methods of this disclosure. The term "antibody" includes polyclonal antibodies and monoclonal antibodies, antibody fragments, as well as derivatives thereof (described above). The antibodies include, but are not limited to mouse, rat, and rabbit or human antibodies. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. The antibodies are also useful to identify and purify therapeutic polypeptides.

Also provided are host cells comprising one or more of the polypeptides or polynucleotides of this disclosure. In one aspect, the polypeptides are expressed and present on the cell surface (extracellularly). Suitable cells containing the disclosed polypeptides include prokaryotic and eukaryotic cells, which include, but are not limited to bacterial cells, yeast cells, insect cells, animal cells, mammalian cells, murine cells, rat cells, sheep cells, simian cells and human cells. Examples of bacterial cells include *Escherichia coli*, *Salmonella enterica* and *Streptococcus gordonii*. The cells can be purchased from a commercial vendor such as the American Type Culture Collection (ATCC, Rockville Maryland, USA) or cultured from an isolate using methods known in the art. Examples of suitable eukaryotic cells include, but are not limited to 293T HEK cells, as well as the hamster cell line CHO, BHK-21; the murine cell lines designated NIH3T3, NSO, C127, the simian cell lines COS, Vero; and the human cell lines HeLa, PER.C6 (commercially available from Crucell) U-937 and Hep G2. A non-limiting example of insect cells include *Spodoptera frupperda*. Examples of yeast useful for expression include, but are not limited to *Saccharomyces, Schizosaccharomyces, Hansenula, Candida, Torulopsis, Yarrowia*, or *Pichia*. See e.g., U.S. Pat. Nos. 4,812,405; 4,818,700; 4,929,555; 5,736,383; 5,955,349; 5,888,768 and 6,258,559.

The present disclosure further provides compositions comprising an antidote of the present disclosure and a pharmaceutically acceptable carrier.

In one embodiment a composition is provided herein, to prevent or reduce bleeding in a subject undergoing anticoagulant therapy with a factor Xa inhibitor comprising an antidote of the present disclosure and a pharmaceutically acceptable carrier.

In another embodiment, compositions are provided that selectively bind and inhibit exogenously administered factor Xa inhibitors in a subject undergoing anticoagulant therapy with a factor Xa inhibitor. The composition is administered to a subject in an effective amount and comprising an antidote of the present disclosure and a pharmaceutically acceptable carrier.

In a further embodiment, the composition is administered to a subject prior to surgery.

"Pharmaceutically acceptable carriers" refers to any diluents, excipients, or carriers that may be used in the compositions of the disclosure. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like, and consistent with conventional pharmaceutical practices.

The pharmaceutical compositions of the disclosure can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The compositions of this disclosure are formulated for pharmaceutical administration to a mammal, preferably a human being. Such pharmaceutical compositions of the disclosure may be administered in a variety of ways, preferably parenterally.

It is contemplated that in order to quickly reverse the anticoagulant activity of a fXa inhibitor present in a patient's plasma in an emergency situation, the antidote of this disclosure can or may be administered to the systemic circulation via parental administration. The term "parenteral" as used herein includes subcutaneous, intravenous, intramuscular, intra-articular, intra-synovial, intrasternal, intrathecal, intrahepatic, intralesional and intracranial injection or infusion techniques. However, in cases where the fXa inhibitor being neutralized has a long plasma half life, a continuous infusion or a sustained release formulation may be required to bind to the fXa inhibitor and such free up the active fXa prior to the clearance of the fXa inhibitor from the body.

Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

In addition to dosage forms described above, pharmaceutically acceptable excipients and carriers and dosage forms are generally known to those skilled in the art and are included in the disclosure. It should be understood that a specific dosage and treatment regimen for any particular patient will depend upon a variety of factors, including the activity of the specific antidote employed, the age, body weight, general health, sex and diet, renal and hepatic function of the patient, and the time of administration, rate of excretion, drug combination, judgment of the treating physician or veterinarian and severity of the particular disease being treated.

XI. Kits

The disclosure further provides kits or packages. In some embodiments, the kit of the present disclosure comprises: (a) a first container containing a fXa inhibitor for regular administration for the treatment of thrombosis, and (b) a second container containing an antidote of this disclosure to be used in cases when there is an overdose of the fXa inhibitor in (a) or when normal hemostasis needs to be restored to stop or prevent bleeding. In other embodiments, the kit further comprises a label explaining when these two agents in (a) and (b) should be used.

The first and second container can be a bottle, jar, vial, flask, syringe, tube, bag, or any other container used in the manufacture, storage, or distribution of a pharmaceutical product. The package insert can be a label, tag, marker, or the like, that recites information relating to the pharmaceutical composition of the kit. The information recited will usually be determined by the regulatory agency governing the area in which the pharmaceutical composition is to be sold, such as the United States Food and Drug Administration. Preferably, the package insert specifically recites the indications for which the pharmaceutical composition has been approved. The package insert may be made of any material on which a person can read information contained therein or thereon. Preferably, the package insert is a printable material, such as paper, adhesive-backed paper cardboard, foil, or plastic, and the like, on which the desired information has been printed or applied.

The disclosure further provides diagnosis kits or packages for in vitro testing. In one embodiment, the kit of the present disclosure comprises a container containing an antidote of this disclosure. The antidote is added to a whole blood or plasma to neutralize fXa inhibitors and thus removes the the interference of the inhibitors with the in vitro testing, such as clotting assays. In some embodiments, the kit of the present disclosure comprises: (a) a first container containing a fXa inhibitor for regular diagnosis testing for the inhibitor, and (b) a second container containing an antidote of this disclosure to determine the effect or guide the use of the antidote.

TABLE 1

Sequence ID NO. 1 - Polypeptide Sequence of Human Factor X

```
  1 MGRPLHLVLL SASLAGLLLL GESLFIRREQ ANNILARVTR ANSFLEEMKK GHLERECMEE
 61 TCSYEEAREV FEDSDKTNEF WNKYKDGDQC ETSPCQNQGK CKDGLGEYTC TCLEGFEGKN
121 CELFTRKLCS LDNGDCDQFC HEEQNSVVCS CARGYTLADN GKACIPTGPY PCGKQTLERR
181 KRSVAQATSS SGEAPDSITW KPYDAADLDP TENPFDLLDF NQTQPERGDN NLTRIVGGQE
241 CKDGECPWQA LLINEENEGF CGGTILSEFY ILTAAHCLYQ AKRFKVRVGD RNTEQEEGGE
301 AVHEVEVVIK HNRFTKETYD FDIAVLRLKT PITFRMNVAP ACLPERDWAE STLMTQKTGI
361 VSGFGRTHEK GRQSTRLKML EVPYVDRNSC KLSSSFIITQ NMFCAGYDTK QEDACQGDSG
421 GPHVTRFKDT YFVTGIVSWG EGCARKGKYG IYTKVTAFLK WIDRSMKTRG LPKAKSHAPE
481 VITSSPLK
```

TABLE 2

Sequence ID NO. 2 - A polynucleotide Sequence Encoding Factor X

```
   1 gactttgctc cagcagcctg tcccagtgag gacagggaca cagtactcgg ccacaccatg
  61 gggcgcccac tgcacctcgt cctgctcagt gcctccctgg ctggcctcct gctgctcggg
 121 gaaagtctgt tcatccgcag ggagcaggcc aacaacatcc tggcgagggt cacgagggcc
 181 aattcctttc ttgaagagat gaagaaagga caccctcgaaa gagagtgcat ggaagagacc
 241 tgctcatacg aagaggcccg cgaggtcttt gaggacagcg acaagacgaa tgaattctgg
 301 aataaataca agatggcga ccagtgtgag accagtcctt gccagaacca gggcaaatgt
 361 aaagacggcc tcggggaata cacctgcacc tgtttagaag gattcgaagg caaaaactgt
 421 gaattattca cacggaagct ctgcagcctg gacaacgggg actgtgacca gttctgccac
 481 gaggaacaga actctgtggt gtgctcctgc gcccgcgggt acaccctggc tgacaacggc
 541 aaggcctgca ttcccacagg gccctacccc tgtgggaaac agaccctgga acgcaggaag
 601 aggtcagtgg cccaggccac cagcagcagc ggggaggccc ctgacagcat cacatggaag
 661 ccatatgatg cagccgacct ggaccccacc gagaacccct tcgacctgct tgacttcaac
 721 cagacgcagc ctgagagggg cgacaacaac ctcaccagga tcgtgggagg ccaggaatgc
 781 aaggacgggg agtgtccctg gcaggccctg ctcatcaatg aggaaaacga gggtttctgt
 841 ggtggaacca ttctgagcga gttctacatc ctaacggcag cccactgtct ctaccaagcc
 901 aagagattca aggtgagggt aggggaccgg aacacggagc aggaggaggg cggtgaggcg
 961 gtgcacgagg tggaggtggt catcaagcac aaccggttca caaaggagac ctatgacttc
1021 gacatcgccg tgctccggct caagaccccc atcaccttcc gcatgaacgt ggcgcctgcc
1081 tgcctccccg agcgtgactg ggccgagtcc acgctgatga cgcagaagac ggggattgtg
1141 agcggcttcg ggcgcaccca cgagaagggc cggcagtcca ccaggctcaa gatgctggag
1201 gtgccctacg tggaccgcaa cagctgcaag ctgtccagca gcttcatcat cacccagaac
```

TABLE 2-continued

Sequence ID NO. 2 - A polynucleotide Sequence Encoding Factor X

```
1261 atgttctgtg ccggctacga caccaagcag gaggatgcct gccaggggga cagcggggc 1321 ccgcacgtca cccgcttcaa ggacacctac ttcgtgacag gcatcgtcag ctggggagag 1381 ggctgtgccc gtaaggggaa gtacgggatc tacaccaagg tcaccgcctt cctcaagtgg 1441 atcgacaggt ccatgaaaac caggggcttg cccaaggcca agagccatgc cccggaggtc 1501 ataacgtcct ctccattaaa gtgagatccc actcaaaaaa aaaaaaaaaa aaaaaaaaa
```

TABLE 3

Sequence ID NO. 3 - Polypeptide Sequence of Mature Human Factor X

```
  1 ANSFLEEMKK GHLERECMEE TCSYEEAREV FEDSDKTNEF WNKYKDGDQC ETSPCQNQGK

61 CKDGLGEYTC TCLEGFEGKN CELFTRKLCS LDNGDCDQFC HEEQNSVVCS CARGYTLADN

121 GKACIPTGPY PCGKQTLERR KRSVAQATSS SGEAPDSITW KPYDAADLDP TENPFDLLDF

181 NQTQPERGDN NLTRIVGGQE CKDGECPWQA LLINEENEGF CGGTILSEFY ILTAAHCLYQ

241 AKRFKVRVGD RNTEQEEGGE AVHEVEVVIK HNRFTKETYD FDIAVLRLKT PITFRMNVAP

301 ACLPERDWAE STLMTQKTGI VSGFGRTHEK GRQSTRLKML EVPYVDRNSC KLSSSFIITQ

361 NMFCAGYDTK QEDACQGDSG GPHVTRFKDT YFVTGIVSWG EGCARKGKYG IYTKVTAFLK

421 WIDRSMKTRG LPKAKSHAPE VITSSPLK
```

TABLE 4

Sequence ID NO. 4 - Polypeptide Sequence of the Gla-domainless Factor Xa lacking 1 to 44 amino acid residues

```
Light Chain
  1                                         KDGDQC ETSPCQNQGK

61 CKDGLGEYTC TCLEGFEGKN CELFTRKLCS LDNGDCDQFC HEEQNSVVCS CARGYTLADN

121 GKACIPTGPY PCGKQTLER

Heavy Chain
181                IVGGQE CKDGECPWQA LLINEENEGF CGGTILSEFY ILTAAHCLYQ

241 AKRFKVRVGD RNTEQEEGGE AVHEVEVVIK HNRFTKETYD FDIAVLRLKT PITFRMNVAP

301 ACLPERDWAE STLMTQKTGI VSGFGRTHEK GRQSTRLKML EVPYVDRNSC KLSSSFIITQ

361 NMFCAGYDTK QEDACQGDSG GPHVTRFKDT YFVTGIVSWG EGCARKGKYG IYTKVTAFLK

421 WIDRSMKTRG LPKAKSHAPE VITSSPLK
```

TABLE 5

Sequence ID NO. 5 Polypeptide Sequence of the Gla-domainless
Factor Xa lacking 1 to 45 amino acid residues Light Chain
```
  1                                              DGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Heavy Chain
```
181              IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDSG GPHVTRFKDT YFVTGIVSWG EGCARKGKYG IYTKVTAFLK
421 WIDRSMKTRG LPKAKSHAPE VITSSPLK
```

TABLE 6

Sequence ID NO. 6-Polypeptide Sequence of Activated Human Factor Xa
prior to Post-Translation of Glutamic Acid to γ-Carboxyglutamic acid Light Chain
```
  1 ANSFLEEMKK GHLERECMEE TCSYEEAREV FEDSDKTNEF WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Heavy Chain
```
181              IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDSG GPHVTRFKDT YFVTGIVSWG EGCARKGKYG IYTKVTAFLK
421 WIDRSMKTRG LPKAKSHAPE VITSSPLK
```

TABLE 7

Sequence ID NO. 7-Polypeptide Sequence of Activated Human Factor Xa
with Post-Translation of Glutamic Acid to γ-Carboxyglutamic acid
(γ represents γ-Carboxyglutamic Acid Residue)

Light Chain
```
  1 ANSFLγγMKK GHLγRγCMγγ TCSYγγARγV FγDSDKTNγF WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Heavy Chain
```
181              IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDSG GPHVTRFKDT YFVTGIVSWG EGCARKGKYG IYTKVTAFLK
421 WIDRSMKTRG LPKAKSHAPE VITSSPLK
```

TABLE 8

Sequence ID NO. 8-Polypeptide Sequence of Activated Human Factor Xa-Light Chain with Post-Translation of Glutamic Acid to γ-Carboxyglutamic acid Light Chain
```
  1 ANSFLγγMKK GHLγRγCMγγ TCSYγγARγV FγDSDKTNγF WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

TABLE 9

Sequence ID NO. 9-Polypeptide Sequence of Activated Human Factor Xa-Heavy Chain

```
181              IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDSG GPHVTRFKDT YFVTGIVSWG EGCARKGKYG IYTKVTAFLK
421 WIDRSMKTRG LPKAKSHAPE VITSSPLK
```

TABLE 10

Sequence ID NO. 10-Polypeptide Sequence of the Des-Gla Anhydro Factor Xa (Ã represents dehydroalanine)

Light Chain
```
  1                                         KDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Heavy Chain
```
181              IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDÃG GPHVTRFKDT YFVTGIVSWG EGCARKGKYG IYTKVTAFLK
421 WIDRSMKTRG LPKAKSHAPE VITSSPLK
```

TABLE 11

Sequence ID NO. 11-Polypeptide Sequence of the Des-Glaf Xa-S379A

Light Chain
```
  1                                          DGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Heavy Chain
```
181              IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

TABLE 12

Sequence ID NO. 12-Polypeptide Sequence of a Human Factor Xa triple mutant prior to removal of the -RKRRKR- (SEQ ID NO. 17) linker Light Chain
```
  1 ANSFL                                      F WNKYKDGDQC ETSPCQNOGK
 61 CKDGLGEYTC TCLEGFEGKN CELFTRKLCS LDNGDCDQFC HEEQNSVVCS CARGYTLADN
121 GKACIPTGPY PCGKQTLER
```
Linker
```
    RKRRKR
```

Heavy Chain
```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

TABLE 13

Sequence ID NO. 13-Polypeptide Sequence of a Human Factor Xa triple mutant after removal of the -RKRRKR- (SEQ ID NO. 17) linker Light Chain
```
  1 ANSFL                                      F WNKYKDGDQC ETSPCQNOGK
 61 CKDGLGEYTC TCLEGFEGKN CELFTRKLCS LDNGDCDQFC HEEQNSVVCS CARGYTLADN
121 GKACIPTGPY PCGKQTLER
```

Heavy Chain
```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

TABLE 13

Linear Polypeptide Numbering of Sequence ID NO. 13a as referenced in the disclosures.

```
             10         20         30         40         50         60
  1 ANSFLFWNKY KDGDQCETSP CQNQGKCKDG LGEYTCTCLE GFEGKNCELF TRKLCSLDNG
 61 DCDQFCHEEQ NSVVCSCARG YTLADNGKAC IPTGPYPCGK QTLERIVGGQ ECKDGECPWQ
121 ALLINEENEG FCGGTILSEF YILTAAHCLY QAKRFKVRVG DRNTEQEEGG EAVHEVEVVI
181 KHNRFTKETY DFDIAVLRLK TPITFRMNVA PACLPERDWA ESTLMTQKTG IVSGFGRTHE
241 KGRQSTRLKM LEVPYVDRNS CKLSSSFIIT QNMFCAGYDT KQEDACQGDA GGPHVTRFKD
301 TYFVTGIVSW GEGCARKGKY GIYTKVTAFL KWIDRSMKTR GLPKAKSHAP EVITSSPLK
```

TABLE 14

Sequence ID NO. 14-Polypeptide Sequence of Light Chain Fragment of Human Factor Xa triple mutant after secretion

```
  1 ANSFL                                      F WNKYKDGDQC ETSPCQNOGK
 61 CKDGLGEYTC TCLEGFEGKN CELFTRKLCS LDNGDCDQFC HEEQNSVVCS CARGYTLADN
121 GKACIPTGPY PCGKQTLER
```

TABLE 15

Sequence ID NO. 15-Polypeptide Sequence of Heavy Chain Fragment of Human Factor Xa triple mutant after secretion

```
Heavy Chain
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

TABLE 16

SEQ ID NO. 16-Polypeptide Sequence of Factor X Gla Domain Delation/Insertion

GLA-Domain Delation/Insertion
1 EEMKK GHLERECMEE TCSYEEAREV FEDSDKTNE

TABLE 17

SEQ ID NO. 17-Light Chain and Heavy Chain Linker

Linker -RKRRKR-

TABLE 18

| Sequence ID NO. 18-A polynucleotide Sequence Encoding r-Antidote (a Factor X triple mutant) | |
|---|---|
| 1 | ATGGGGCGCC CACTGCACCT CGTCCTGCTC AGTGCCTCCC TGGCTGGCCT CCTGCTGCTC GGGGAAAGTC TGTTCATCCG CAGGGAGCAG GCCAACAACA |
| 101 | TCCTGGCGAG GGTCACGAGG GCCAATTCCT TTCTTTTCTG GAATAAATAC AAAGATGGCG ACCAGTGTGA GACCAGTCCT TGCCAGAACC AGGGCAAATG |
| 201 | TAAAGACGGC CTCGGGGAAT ACACCTGCAC CTGTTTAGAA GGATTCGAAG GCAAAAACTG TGAATTATTC ACACGGAAGC TCTGCAGCCT GGACAACGGG |
| 301 | GACTGTGACC AGTTCTGCCA CGAGGAACAG AACTCTGTGG TGTGCTCCTG CGCCCGCGGG TACACCCTGG CTGACAACGG CAAGGCCTGC ATTCCCACAG |
| 401 | GGCCCTACCC CTGTGGGAAA CAGACCCTGG AACGCAGGAA GAGGAGGAAG AGGATCGTGG GAGGCCAGGA ATGCAAGGAC GGGGAGTGTC CCTGGCAGGC |
| 501 | CCTGCTCATC AATGAGGAAA ACGAGGGTTT CTGTGGTGGA ACCATTCTGA GCGAGTTCTA CATCCTAACG GCAGCCCACT GTCTCTACCA AGCCAAGAGA |
| 601 | TTCAAGGTGA GGGTAGGGGA CCGGAACACG GAGCAGGAGG AGGGCGGTGA GGCGGTGCAC GAGGTGGAGG TGGTCATCAA GCACAACCGG TTCACAAAGG |
| 701 | AGACCTATGA CTTCGACATC GCCGTGCTCC GGCTCAAGAC CCCCATCACC TTCCGCATGA ACGTGGCGCC TGCCTGCCTC CCCGAGCGTG ACTGGGCCGA |
| 801 | GTCCACGCTG ATGACGCAGA AGACGGGGAT TGTGAGCGGC TTCGGGCGCA CCCACGAGAA GGGCCGGCAG TCCACCAGGC TCAAGATGCT GGAGGTGCCC |
| 901 | TACGTGGACC GCAACAGCTG CAAGCTGTCC AGCAGCTTCA TCATCACCCA GAACATGTTC TGTGCCGGCT ACGACACCAA GCAGGAGGAT GCCTGCCAGG |
| 1001 | GGGACGCAGG GGGCCCGCAC GTCACCCGCT TCAAGGACAC CTACTTCGTG ACAGGCATCG TCAGCTGGGG AGAGGGCTGT GCCCGTAAGG GGAAGTACGG |
| 1101 | GATCTACACC AAGGTCACCG CCTTCCTCAA GTGGATCGAC AGGTCCATGA AAACCAGGGG CTTGCCCAAG GCCAAGAGCC ATGCCCCGGA GGTCATAACG |
| 1201 | TCCTCTCCAT TAAAGTGA |

TABLE 19

Sequence ID. NO. 19-Polynucleotide Sequence of the r-Antidote Expression Vector

```
   1 TCTAGACACA GTACTCGCGC ACACCATGGG GCGCCCCACTG CACCTCAGTGC TGCTCAGTGCC CTCCCTGGCT GGCCTCCTGC TGCTCGGGGA AAGTCTGTTC
 101 ATCCCAGGG AGCAGGCCAA CAACATCCTG GCGAGGGTCA CGAGGCCCAA TTCCTTTCTT TCTGGAATA AATACAAAGA TGGCGACCAG TGTGAGACCA
 201 GTCCTTGCCA GAACCAGGGC AAATGTAAAG ACGGCCTCCG GGAATACACC TGCACCTGTT TAGAAGGATT CGAAGGCAAA AACTGTGAAT TATTCACACG
 301 GAAGCTCTGC AGCCTGGACA ACGGGACTG TGACCAGTTC TGCCACAGAG AACAGAATC TGTGGTGTCC TCCTGCGCCC GCGGGTACAC CCTGGCTGAC
 401 AACGGCAAGG CCTGCATTCC CACAGGCTGC CTACCCCTGT GGAAACAGAC CCTGGAACGC AGGAAGAGGA GGAAGAGGAT TCTGAGCGAG CGTGGGAGGC
 501 AGGACGGGGA GTGTCCCTGC GTGTGCCTGG CAGGCCCTGC GTGAGGGTA ACACGGAGCA GGTTTCTGTG GTGAACCAT TCTGAGCGAG TGCAGGT
 601 CCACTGTCTC TACCAAGCA AGAGATTCAA TATGACTTCAC AAAGGAGACC GTCTGAGGCT GTCCGAGCA ACACGGAGCG GGTAGGAGGC TCACCTTCCG CATGAACGTG GCGCCTCCT
 701 ATCAAGCACA ACCGGTTCAC AAAGGAGACC TATGACTTCAC AAAGGAGACC TATGACTTCAC ACATCGCGGT GTCCGAGCCA AAGACCCCCA TCACCTTCCG CATGAACGTG GCGCCTCCT
 801 GCCTCCCCGA GCGTGACTGG GCCGAGTCCA CGCTGATGAC GCAGAAGACG GGGATTGTGA GCCTTGTCCG GCCCACCCAC CCCACCCAC CGGCAGTCAC GGCAGTCCAC
 901 CAGGCTCAAG ATGCTGGAGG TGCCCTACGT GGACCGCAAC AGCTGCAAGC TGTCCAGCAG CTTCATCATC ACCCAGAACA TGTTCTGTGC CGGTACGAC
1001 ACCAAGCAGG CCAAGGCCTG CCAGGGGGAC TGCCAGGGCG ATAGTGGGGG GCCACCTACT CCGTACAGG GACACCTACT TCTGACAGG CATCGTCAGC CCAAGGCCAA
1101 GCTGTGCCCG TAAGGGGACA TACGGGCTTT ACACCAAGGT CCTGGCCTCC GAGAAGAACG CTTCAAGTA CTTCAAGTA CATGAAAACC AGGGCTTGC CCAAGGCCAA
1201 GAGCCATGCC CCGGAGGTCA TAACGCTCTC TCCATTAAAG TGCCCTCCCG GCCCCTCCCC GCCCATCCCC AGGTTCACCTTG TGTCACCTAC AGGTGCCAC ATGCTAGAGC TCGCTGATCA
1301 GCCTCGACTG TGCCAGCCA TCTGTGTGTT TTGCAGCTGA CCTCGCCTGG GGGTGGGG CAGCAGGGA CAGCAAGGGG GAGGATTGGG AAGACAATAG
1401 AAAATGAGGA AATTGCATCG AATTGCATCG GCTTACCAGA AGCATGAAT CAACCAGGCC ACCTTAGACT CTTTGTGACA AGGAATTGA AGGAATTGA AAGCATGAAT AAGCATGAAT
1501 CAGGCAGTGT GGGGATGGG TGGCTCTCAT AAACTTCTCC CAGAATACCC AGGGCTTCTC CAGCAGCGG CGCCCCTCT GAGGGCGAAA GAACCAGCTG TATAAGTTTG
1601 TGGAATGTGT GTCAGTTAGG AAATGATT GGGGAAATAT ATGCTTTCAA CAGAGATG GATGACA GATGACTTCAC GCAAAGAGC CATATGTCC GCCCATCC AGGTGTGGAA
1701 AGTCCCCAGG CTCCCCAGCA GGCAGGAGTA TGCAAGCAT TGGCTGACTA TTTATTTTTA TAGTCAGA TTTATGCAGA TGGCTGAGCC GCTGAGTATT CCGGCCATCC
1801 TCCGCCCAGT CTCCGCCCAT TGGCTGACTA TGGCTGACTA CTAGCTCCA CTAGCTCCAC TGGCCGAGGC ATTGCCAC ATTGAACTGC ATCGTCGCCG TGCTCCAAA
1901 TCGAGAGCAT TTTTTTGGAG CCTAGGGTT GCCAAAAAG GCTAGCTCCC GCTGCCATCA AGTTCAAGTA CTTTCAAAGA ATGACCACA ATGACCACA GGAAGTAAA
2001 TATGGGGATT GGCAAGAACG GAGACCTACC CTGGCCTTCG GAGTTCAAGTA TTAAAGGACA GAATTAATAT AGTTCTAGT AGAGAACTCA
2101 CAGAATCTGG TGATTATGGG TAGGAAAACC TGGTTCCCAA CAAAGTTT GGATGATGCC TTAAGACTTA TGAACACC GGAATTGCA AGTAAGTAG ACATGTTTG
2201 AAGACCACC ACAGGAGAGT CATTTTTTCTG CCAATGAAT AACAGGCC ACCTGAGCT CTTTGTGACA CTTTGTGACA AGGATCATGC AAGTGACACG
2301 GATAGTTCGGA TTTACCAGGA GTATCTCAAT AGCATGCAAT AGCTAGACT CCTTAGACT CTTTGTGACA CAGCGAGCA AGGAATTTGA AGGAATTGA AGGCATGAAT TATAAGTTTG
2401 TTTTTCCAG AAATGATT GGGGAAATAT AAACTTCTCC CAGAATACCC AGGGCTTCTC CAGCAGCGG CGCCCCTCT GAGGGCGAAA GAACCAGCTG TATAAGTTTG
2501 AAGTCTACGA GAAGAAAGAC ATGCTTTCAA GCATTCAAT GTTCTCTGCT CCCCTCCCTAA CAAACCACAA ATACGAGCCG ACCTGTCGTG GAAGCATAAA GTGTAAAGCC TTTGCTGCT
2601 TTAGATCCCG CGGAGATCCA GACATGATAA TGAGTTTGGA CAAACCACAA ACAACAACAA TTGCATTCAT TTTATGTTTC AGGTTCAGGG CCAGTCGCAT TAATGAATCG GCCAACGCGC
2701 TGATGCTATT GCTTTATTTG TAACCATTAT AAGCTGCAAT AAACAAGTTA ACAACAACAA TTGCATTCAT CGGTTCGTT CGGTTCGTT CGGTCCGCC GAGCGGTATC AGCTCACTCA
2801 GAGGTTTTTT AAGCAACTAA AAACCTTCAT AAATGTCGTA TGGCTGATTA TGCACCTTGT CTTTGTTCC CTTTAGTGAG GGTTAATTGC GCGCTTGGCG TAATCATGGT
2901 TAATCATGGT CATAGCTGTT TCCTGTGTGA TTAATTGCGT TGCGCTCACT GCCCGCTTTC CAGTCGGGAA ACCTGTCGTG CCAGCTGCAT TAATGAATCG GCCAACGCGC
3001 AATAGTGAG CTAACTCACA TTAATTGCGT TGCGCTCACT GCCCGCTTTC CAGTCGGGAA ACCTGTCGTG CCAGCTGCAT TAATGAATCG GCCAACGCGC
3101 GGGGAGAGGC GGTTTGCGTA TTGGGCGCTC TTCCGCTTCC TCGCTCACTG ACTCGCTGCG CTCGGTCGTT CGGCTGCGGC GAGCGGTATC AGCTCACTCA
3201 AAGGCGGTAA CAGCAATCA CAGGAAAGAA CATGTGAGCA AAAGGCCAGC AAAAGGCCAG GAACCGTAAA AAGGCCGCGT TGCTGGCGTT TTTCCATAGG
3301 TCGTGCCGTT TTTCCATAGG CTCCGCCCCC CTGACGAGCA TCACAAAAAT CGACGCTCAA GTCAGAGGTG GCGAAACCCG ACAGGACTAT AAAGATACCA
3401 GGCGTTTCCC CCTGGAAGCT CCCTCGTGCG CTCTCCTGTT CCGACCCTGC CGCTTACCGG ATACCTGTCC GCCTTTCTCC CTTCGGGAAG CGTGGCGCTT
3501 TCTCATAGCT CACGCTGTAG GTATCTCAGT TCGGTGTAGG TCGTTCGCTC CAAGCTGGGC TGTGTGCACG AACCCCCCGT TCAGCCCGAC CGCTGCGCCT
3601 TATCCGGTAA CTATCGTCTT GAGTCCAACC CGGTAAGACA CGACTTATCG CCACTGGCAG CAGCCACTGG TAACAGGATT AGCAGAGCGA GGTATGTAGG
3701 CGGTGCTACA GAGTTCTTGA AGTGGTGGCC TAACTACGGC TACACTAGAA GAACAGTATT TGGTATCTGC GCTCTGCTGA AGCCAGTTAC CTTCGGAAAA
3801 AGAGTTGGTA GCTCTTGATC CGGCAAACAA ACCACCGCTG GTAGCGGTGG TTTTTTTGT TTGCAAGCAG CAGATTACGC GCAGAAAAAA GGATCTCAAG
3901 AAGATCCTTT GATCTTTTCT ACGGGGTCTG ACGCTCAGTG GAACGAAAAC TCACGTTAAG GGATTTTGGT CATGAGATTA TCAAAAAGGA TCTTCACCTA
4001 GATCCTTTTA AATTAAAAAT GAAGTTTTAA ATCAATCTAA AGTATATATG AGTAAACTTG GTCTGACAGT TACCAATGCT TAATCAGTGA GGCACCTATC
4101 TCAGCGATCT GTCTATTTCG TTCATCCATA GTTGCCTGAC TCCCCGTCGT GTAGATAACT ACGATACGGG AGGGCTTACC ATCTGGCCCC AGTGCTGCAA
4201 TGATACCGCG AGACCCACGC TCACCGGCTC CAGATTTATC AGCAATAAAC CAGCCAGCCG GAAGGGCCGA GCGCAGAAGT GGTCCTGCAA CTTTATCCGC
4301 CTCCATCCAG TCTATTAATT GTTGCCGGGA AGCTAGAGTA AGTAGTTCGC CAGTTAATAG TTTGCGCAAC GTTGTTGCCA TTGCTACAGG CATCGTGGTG
4401 TCAAAGACTC CGTTTGGTAT GGCTTCATTC AGCTCCGGTT CCCAACGATC AAGGCGAGTT ACATGATCCC CCATGTTGTG CAAAAAAGCG GTTAGCTCCT
4501 TCGGTCCTCC GATCGTTGTC AGAAGTAAGT TGGCCGCAGT GTTATCACTC ATGGTTATGG CAGCACTGCA TAATTCTCTT ACTGTCATGC CATCCGTAAG
4601 ATGCTTTTCT GTGACTGGTG AGTACTCAAC CAAGTCATTC TGAGAATAGT GTATGCGGCG ACCGAGTTGC TCTTGCCCGG CGTCAATACG GGATAATACC
4701 GCGCCACATA GCAGAACTTT AAAAGTGCTC ATCATTGGAA AACGTTCTTC GGGGCGAAAA CTCTCAAGGA TCTTACCGCT GTTGAGATCC AGTTCGATGT
4801 AACCCACTCG TGCACCCAAC TGATCTTCAG CATCTTTTAC TTTCACCAGC GTTTCTGGGT GAGCAAAAAC AGGAAGGCAA AATGCCGCAA AAAAGGGAAT
```

TABLE 19 -continued

Sequence ID. NO. 19-Polynucleotide Sequence of the r-Antidote Expression Vector

```
4901 AAGGGCGACA CGGAAATGTT GAATACTCAT ACTCTTCCTT TTTCAATATT ATTGAAGCAT TTATCAGGGT TATTGTCTCA TGAGCGGATA CATATTTGAA
5001 TGTATTTAGA AAAATAAACA AATAGGGGTT CCGCGCACAT TCCCCGAAA AGTGCCACCT GGGAAATTGT AAACGTTAAT ATTTTGTTAA AATTCGCGTT
5101 AAATTTTTGT TAAATCAGCT CATTTTTTAA CCAATAGGCC GAAATCGGCA AAATCCCTTA TAAATCAAAA GAATAGACCG AGATAGGGTT GAGTGTTGTT
5201 CCAGTTTGGA ACAAGAGTCC ACTATTAAAG AACGTGGACT CCAACGTCAA AGGCGCAAAA ACCGTCTATC AGGGCGATGG CCCACTACGT GAACCATCAC
5301 CCTAATCAAG TTTTTTGGGG TCGAGGTGCC GTAAAGCACT GTAAAGGGA CCTAAAGGGA GCCCCCGATT TAGAGCTTGA CGGGGAAAGC CGGCAACGT
5401 GGCGAGAAAG GAAGGGAAGA AGCGAAAGG AGCGGCGCT CCATTCAGGC TGCGCAACTG CAAGTGTAGC GGTCACGCTG CGCGTAACCA CCACACCCGC CGCGCTTAAT
5501 GCGCCGCTAC AGGGCGCGTC GCGCCATTCG CGATTAAGTT CCATTCAGGC TGCGCAACTG TTGGGAAGGG CGATCGGTGC GGGCCTCTTC GCTATTACGC CAGTGGCGA
5601 ACTATATGCG GAATTGGAAT TAATTCGCTG GGCTGAGACC CGCAGAGGAA CAGCGCTCTAG GGATTTGTCC CGACTAGCG AGATGGCAAG GCTGAGGACG
5701 GGAGGCTGAT TGAGAGGCGA AGTACACCC TAATCTCAAT ACAACCCTTG GAGCTAAGCC AGCAATGGTA GAGGGAAGAT TCTGCACGTC CCTTCCAGGC
5801 GGCCTCCCCG TCACCACCA CCCCAACCCG ATCGCTCTT TCCCGCCCCC GTCTCGTCA AAAGGACTCG CCCCTGCCTT GGGGAATCCC AGGACCGTC
5901 GTTAAACTCC CACTAACGTA GAACCCAGAG ATCGCTGCGT TCCCGCCCCA GTCCCGAGA AGTTGGGGG AGGGGTCGC AATTGAACCG GTGCCTAGAG AAGGTGGCGC
6001 CTCCGGTGCC CGTCAGTGGG CAGAGCGCAC ATCGCCCACA GTCCCGAGA AGTTGGGGG AGGGGTCGC GAACCGTATA TAAGTGCAGT AGTCGCCGTG AACGTTCTTT
6101 GGGGTAAACT GGGAAAGTGA TGTCGTGTAC TGGCTCCGCC TTTTTCCGA GGGTGGGGA CGCGGGCCTG GCTCTTTTAC GGGTTATGCC CCTTGCGTGC CTTGAATTAC
6201 TTGCAAACGG GTTTGCCCGC AGAACACAGG TAAGTGCCGT GTGTGGTTCC CGCGGGGTT GAAAGTGGGT GGGAGAGTTC GAGGCCTTGC TATCTCGCTG CCCCTTCGCC
6301 TTCCACGCCC CTGGCTGCAG TACGTGATTC TTGATCCCGA GCTTCGGGGT CTGGGGCGAA CTTCGCGCC TATCTCGCTG CTTTCGATAA GTCTCTAGCC
6401 TCGTGTTGA GTTGAGGCCT GGCTGGGGGG CTGGGGCGCG CTGGGGCGAC TCTTGTAAAT GCGGCCAAG ATCTGCACAC TGGTATTTCG GTTTTTGGGG
6501 ATTTAAAATT TTTGATGACC TGCTGCGACG CTTTTTTTCT AGCGCACATG CGGGCCTGC GAGCGCGGCA ACCGAGAATC GGACGGGGGT AGTCTCAAGC
6601 CCGCGGGCCG CGACGGGGCC GTGCGTCCC AGCGCAGCA CGGGCCTGC GAGCGCGGCA ACCGAGAATC AAGGCTGGCC CGTCGGCAC CAGTCGCGTG AGCGAAAGA
6701 TGGCCGGCCT GCTCGGTGC CTGGCCTGC GCCGCCGTGT ATCGCCGC CTCGGAGAG GGTGCGGGGT AGTCACCCAC ACAAAGGAAA AGGGCTTTC
6801 CGTCCTTCAG CCGGCCCTTGC CCGAGGAGC TCAAATGGA GGACGGGGTG CTCGGAGAG AAGGCTGGCC ATTAGTTCTC GAGCTTTTGG AGTACGTCGT CTTTAGGTTG
6901 GGGAGGGGG TTTTATGCAA TGGAGTTTCC CCACACTGAG TGGGTGGAGA CTGAAGTTAG GCCAGCTTGG CACTTGATGT AATTCTCCTT GGAATTGCC
7001 CTTTTTGAGT TTGATCTTG GTCATTCTC AAGCCTCAGA CAGTGGTTCA AAGTTTTTTT CTTCCATTC AGTGTCGTG CTAAAAGCCA
7201 AAT
```

EXAMPLES

The disclosure is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings:

aa=amino acid
ab=antibody
ACT=activated clotting time
aPTT=activated partial thromboplastin time
CHO cell=Chinese hamster ovary cell
CHO dhfr(−)cells=CHO cells lacking dhfr gene
fXa=factor Xa
hr=hour
INR=international normalized ratio
IV=intravenous
kg=kilogram
M=molar
mg=milligram
mg/kg=milligram/kilogram
mg/mL=milligram/milliliter
min=minute
mL=milliliter
mM=millimolar
nm=nanometer
nM=nanomolar
PO=oral
PRP=platelet rich plasma
PT=prothrombin time
RFU=relative fluorescence unit
s=second
TF=tissue factor
U/mL=units/milliliter
μL or uL=microliter
μM=micromolar
μg=microgram

Example 1. Thrombin Generation Assay in Platelet Poor Plasma (PPP) or Platelet Rich Plasma (PRP)

In this example, human platelet poor or platelet rich plasma samples were prepared from blood of healthy donors drawn into 0.32% citrate. PRP and PPP were prepared by spinning the anticoagulated blood at ~100× gravity or 1000× gravity for 20 minutes, respectively, at room temperature. 75-100 microliter (uL) plasma was mixed with CaCl$_2$) and Z-Gly-Gly-Arg-aminomethylcoumarin (Z-GGR-AMC, a thrombin fluorogenic substrate). Tissue factor (Innovin, Dade Behring) was added to initiate the generation of thrombin. For a typical experiment, the reaction mixture contained 15 millimolar (mM) Ca$^{2+}$, 100 micromolar (μM) Z-GGR-AMC, and 0.1 nanomolar (nM) tissue factor (TF) (Innovin). Thrombin formation was monitored continuously at 37° C. by a fluorometric plate reader (Molecular Devices) measuring the relative fluorescence units (RFU). Inhibitor and antidote, when present, were pre-incubated with plasma for 20 minutes at room temperature before initiation of thrombin generation.

Example 2. Clotting Prolongation Assays

Two clotting assay formats were used to test the effects of factor Xa inhibitors and the antidote on clotting prolongation. In the first format, a 96-well plate was used to measure multiple samples at the same time. In the second assay format, aPTT was measured with a conventional coagulation instrument (MLA Electra 800 automatic coagulation timer).

In the 96-well plate format method, human platelet poor plasma or platelet rich plasma was prepared similarly as procedures in Example 2. 75-100 μL plasma was recalcified with CaCl$_2$), incubated at 37° C. for 3 minutes and clot formation was initiated by adding tissue factor (Innovin, Dade Behring) or an aPTT reagent (Actin F S, Dade Behring). Change of OD405 was monitored continuously by a plate reader (Molecular Devices). Clotting time was defined as the time (second) when the half maximal value of absorbance (OD405 nm) change was reached. Factor Xa inhibitor and antidote, when present, were pre-incubated with plasma at room temperature for 20 minutes before initiation of the reaction.

When an active fXa was tested for its clotting activity, 75-100 uL fX deficient plasma (George King Bio-Medical, Inc.) was recalcified with CaCl$_2$, incubated at 37° C. for 3 minutes and fXa products following chymotrypsin digestion was added to the plasma to initiate clot formation. Change of OD405 was continuously monitored by a plate reader as described before.

Example 3. Expression of Recombinant Antidotes in CHO Cells

In this example, antidote mutants can be directly expressed in CHO cells and functional proteins are purified from conditioned medium as described below. Recombinant antidotes' functional activity can be tested in vitro and in animal model.

DNA sequences encoding the antidotes described herein can be sequenced and inserted to an expression vector. The vector can then be linearized and transfected into CHO dhfr(−) cells. Cells are selected using tetrahydrofolate (HT) deficient media plus methotrexate (MTX). Stable clones are screened for high protein expression using a fX ELISA kit (Enzyme Research Laboratories, Catalogue Number FX-EIA). Antidotes are expressed in serum free medium and conditioned medium is harvested and processed for purification.

Target protein in the conditioned medium can be isolated by ion exchange chromatography and subsequently purified by single step affinity chromatography (such as an anti-fXa antibody coupled to a matrix) or by a combination of several chromatography steps such as hydrophobic and size exclusion matrices. The affinity purifications may include chromatographic material that selectively binds to fXa active site cleft, such as benzamidine-sepharose or soybean trypsin inhibitor-agarose (STI-Agarose).

Example 4. Reversal of Inhibition of fXa by Antidotes

To measure the inhibition of fXa activity by betrixaban and reversal of its inhibitory effect, purified active fXa, different concentrations of betrixaban and different antidotes of the present disclosure can be added to 20 mM Tris, 150 mM NaCl, 5 mM $Ca^{2+}$, and 0.1% Bovine Serum Albumin (BSA). After incubation at room temperature for 20 minutes, 100 µM Spectrozyme-fXa (a factor Xa chromogenic substrate, American Diagnostica) is added to the mixture and the rate of substrate cleavage is monitored continuously for 5 minutes at 405 nanometer (nm) by a plate reader. The chromogenic activity is normalized to active fXa in the absence of any inhibitor. Initial velocity of product formation as a function of inhibitor and antidote concentration is analyzed by nonlinear regression to estimate the affinity of betrixaban to the antidote.

The effect of the antidotes on thrombin activity toward a chromogenic substrate S2288 (200 µM) is measured similarly as before with or without Argatroban, a specific small molecule IIa inhibitor.

Example 5. In Vivo Mouse Model

The pharmacokinetic and pharmacodynamic (PK-PD) profile of betrixaban in male C57Bl/6 mice with or without administrating antidote are tested. Single oral administration of betrixaban is dosed at 0, 15, 25, and 75 mg/kg for controls groups. 15 mg/kg is used for antidote treated group. A single intravenous (IV) injection of antidote (300 ug/200 µL) or vehicle (normal saline, 200 µL) is administered 5 minutes prior to the 1.5 hr. time point.

At 1.5, 2.0, and 4.0 hrs following oral administration of betrixaban, mice are anesthetized with a ketamine cocktail (SC) and exsanguinated via cardiac puncture. Blood samples (0.5 mL) are obtained in 50 µL trisodium citrate. Whole blood INR is measured using Hemochron Jr. cartridges (International Technidyne Corporation) per the manufacturer's instructions. Mouse platelet poor plasma is prepared by centrifugation for betrixaban and antidote (ELISA) plasma concentration determinations.

For antidotes experiments, mice are orally dosed with betrixaban at 0, 15, 25, and 75 mg/kg for control groups. 15 mg/kg is used for antidote (300 µg/200 µL) treated group. Samples are taken at 1.5 hr after oral administration of betrixaban (5 min. following antidote injection).

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. An isolated two-chain polypeptide comprising the amino acid sequence of SEQ ID NO. 13 which further comprises at least one mutation, as compared to SEQ ID NO. 13, selected from the group consisting of:
  (i) D12E, D29E, N59Q, N71Q, N71S, N71A, N86Q, N86S, D114E, D114S, N163S, N163Q, N259Q, N259S, and N259A,
  (ii) V232I, D284M, D284Q, D284S, V308S, G311H, G311K, G311N, G311Q, and G311S, and
  (iii) A290N, A290Q, A290K, H147S, H147T, H147N, H147Q, and D193N.

2. The polypeptide of claim 1, wherein the at least one mutation is selected from the group consisting of N86Q, N86S, D114E, and D114S.

3. The polypeptide of claim 1, wherein the at least one mutation is selected from the group consisting of:
  i) D284M;
  ii) D284M and G311S;
  iii) D284M, V232I, and V308S;
  iv) D284M, G311S, V232I, and V308S;
  v) D284Q;
  vi) D284Q and G311S;
  vii) D284Q, V232I, and V308S;
  viii) D284Q, G311S, V232I, and V308S;
  ix) D284S and G311Q;
  x) D284S, G311Q, V232I, and V308S;
  xi) G311K;
  xii) G311Q;
  xiii) G311N;
  xiv) G311S;
  xv) G311H;
  xvi) G311K, V232I, and V308S;
  xvii) G311Q, V232I, and V308S;
  xviii) G311N, V232I, and V308S;
  xix) G311S, V232I, and V308S; and
  XX) G311H, V232I, and V308S.

4. The polypeptide of claim 1, wherein the at least one mutation is selected from the group consisting of:
  i) A290N;
  ii) A290Q;
  iii) A290K;
  iv) H147S;
  v) H147T;
  vi) H147N;
  vii) H147Q;
  viii) H147S and D193N;
  ix) H147T and D193N;
  x) H147N and D193N; or combinations thereof.

* * * * *

SEQUENCE LISTING

<160> NUMBER OF SEQ ID NOS: 23

<210> SEQ ID NO 1
<211> LENGTH: 488
<212> TYPE: PRT
<213> ORGANISM: Homo sapiens

<400> SEQUENCE: 1

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205
```

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 2
<211> LENGTH: 1560
<212> TYPE: DNA
<213> ORGANISM: Homo sapiens

<400> SEQUENCE: 2
gactttgctc cagcagcctg tcccagtgag gacagggaca cagtactcgg ccacaccatg    60
gggcgcccac tgcacctcgt cctgctcagt gcctccctgg ctggcctcct gctgctcggg   120
gaaagtctgt tcatccgcag ggagcaggcc aacaacatcc tggcgagggt cacgagggcc   180
aattcctttc ttgaagagat gaagaaagga cacctcgaaa gagagtgcat ggaagagacc   240
tgctcatacg aagaggcccg cgaggtcttt gaggacagcg acaagacgaa tgaattctgg   300
aataaataca agatggcgga ccagtgtgag accagtcctt gccagaacca gggcaaatgt   360
aaagacggcc tcgggggaata cacctgcacc tgtttagaag gattcgaagg caaaaactgt   420
gaattattca cacggaagct ctgcagcctg gacaacgggg actgtgacca gttctgccac   480

```
gaggaacaga actctgtggt gtgctcctgc gcccgcgggt acaccctggc tgacaacggc      540
aaggcctgca ttcccacagg gccctacccc tgtgggaaac agaccctgga acgcaggaag      600
aggtcagtgg cccaggccac cagcagcagc ggggaggccc ctgacagcat cacatggaag      660
ccatatgatg cagccgacct ggaccccacc gagaacccct cgacctgct tgacttcaac       720 cagacgcagc tgagagggg cgacaacaac ctcaccagga tcgtgggagg ccaggaatgc      780 aaggacggg agtgtccctg caggccctg ctcatcaatg aggaaaacga gggtttctgt       840
ggtggaacca ttctgagcga gttctacatc ctaacggcag cccactgtct ctaccaagcc     900
aagagattca aggtgaggt aggggaccgg aacacggagc aggaggaggg cggtgaggcg      960
gtgcacgagg tggaggtggt catcaagcac aaccggttca caaaggagac ctatgacttc    1020
gacatcgccg tgctccggct caagacccc atcaccttcc gcatgaacgt ggcgcctgcc     1080
tgcctccccg agcgtgactg ggccgagtcc acgctgatga cgcagaagac ggggattgtg    1140
agcggcttcg gcgcacccca cgagaagggc cggcagtcca ccaggctcaa gatgctggag    1200
gtgccctacg tggaccgcaa cagctgcaag ctgtccagca gcttcatcat cacccagaac    1260
atgttctgtg ccggctacga caccaagcag gaggatgcct gccaggggga cagcggggc     1320 ccgcacgtca cccgcttcaa ggacacctac ttcgtgacag catcgtcag ctggggagag     1380 ggctgtgccc gtaaggggaa gtacgggatc tacaccaagg tcaccgcctt cctcaagtgg    1440
atcgacaggt ccatgaaaac caggggcttg cccaaggcca agagccatgc cccggaggtc    1500
ataacgtcct ctccattaaa gtgagatccc actcaaaaaa aaaaaaaaa aaaaaaaaa      1560
```

<210> SEQ ID NO 3
<211> LENGTH: 448
<212> TYPE: PRT
<213> ORGANISM: Homo sapiens

<400> SEQUENCE: 3

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
                20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
        50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
                100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg Arg Lys Arg Ser Val
        130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190
```

```
Thr Arg Ile Val Gly Gly Gln Glu Cys Lys Asp Gly Glu Cys Pro Trp
            195                 200                 205

Gln Ala Leu Leu Ile Asn Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Ile Lys His Asn
            260                 265                 270

Arg Phe Thr Lys Glu Thr Tyr Asp Phe Asp Ile Ala Val Leu Arg Leu
                275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
                355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
    435                 440                 445

<210> SEQ ID NO 4
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Lys Asp Gly Asp Gln Cys Glu Thr Ser Pro Cys Gln Asn Gln Gly Lys
1               5                   10                  15

Cys Lys Asp Gly Leu Gly Glu Tyr Thr Cys Thr Cys Leu Glu Gly Phe
                20                  25                  30

Glu Gly Lys Asn Cys Glu Leu Phe Thr Arg Lys Leu Cys Ser Leu Asp
            35                  40                  45

Asn Gly Asp Cys Asp Gln Phe Cys His Glu Glu Gln Asn Ser Val Val
    50                  55                  60

Cys Ser Cys Ala Arg Gly Tyr Thr Leu Ala Asp Asn Gly Lys Ala Cys
65                  70                  75                  80

Ile Pro Thr Gly Pro Tyr Pro Cys Gly Lys Gln Thr Leu Glu Arg Ile
                85                  90                  95

Val Gly Gly Gln Glu Cys Lys Asp Gly Glu Cys Pro Trp Gln Ala Leu
```

```
            100                 105                 110
Leu Ile Asn Glu Glu Asn Glu Gly Phe Cys Gly Gly Thr Ile Leu Ser
            115                 120                 125

Glu Phe Tyr Ile Leu Thr Ala Ala His Cys Leu Tyr Gln Ala Lys Arg
            130                 135                 140

Phe Lys Val Arg Val Gly Asp Arg Asn Thr Glu Gln Glu Glu Gly Gly
145                 150                 155                 160

Glu Ala Val His Glu Val Glu Val Val Ile Lys His Asn Arg Phe Thr
                165                 170                 175

Lys Glu Thr Tyr Asp Phe Asp Ile Ala Val Leu Arg Leu Lys Thr Pro
            180                 185                 190

Ile Thr Phe Arg Met Asn Val Ala Pro Ala Cys Leu Pro Glu Arg Asp
            195                 200                 205

Trp Ala Glu Ser Thr Leu Met Thr Gln Lys Thr Gly Ile Val Ser Gly
            210                 215                 220

Phe Gly Arg Thr His Glu Lys Gly Arg Gln Ser Thr Arg Leu Lys Met
225                 230                 235                 240

Leu Glu Val Pro Tyr Val Asp Arg Asn Ser Cys Lys Leu Ser Ser Ser
                245                 250                 255

Phe Ile Ile Thr Gln Asn Met Phe Cys Ala Gly Tyr Asp Thr Lys Gln
            260                 265                 270

Glu Asp Ala Cys Gln Gly Asp Ser Gly Gly Pro His Val Thr Arg Phe
            275                 280                 285

Lys Asp Thr Tyr Phe Val Thr Gly Ile Val Ser Trp Gly Glu Gly Cys
            290                 295                 300

Ala Arg Lys Gly Lys Tyr Gly Ile Tyr Thr Lys Val Thr Ala Phe Leu
305                 310                 315                 320

Lys Trp Ile Asp Arg Ser Met Lys Thr Arg Gly Leu Pro Lys Ala Lys
                325                 330                 335

Ser His Ala Pro Glu Val Ile Thr Ser Ser Pro Leu Lys
            340                 345

<210> SEQ ID NO 5
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Glu Gly Phe Glu
            20                  25                  30

Gly Lys Asn Cys Glu Leu Phe Thr Arg Lys Leu Cys Ser Leu Asp Asn
        35                  40                  45

Gly Asp Cys Asp Gln Phe Cys His Glu Glu Gln Asn Ser Val Val Cys
    50                  55                  60

Ser Cys Ala Arg Gly Tyr Thr Leu Ala Asp Asn Gly Lys Ala Cys Ile
65                  70                  75                  80

Pro Thr Gly Pro Tyr Pro Cys Gly Lys Gln Thr Leu Glu Arg Ile Val
                85                  90                  95

Gly Gly Gln Glu Cys Lys Asp Gly Glu Cys Pro Trp Gln Ala Leu Leu
            100                 105                 110
```

Ile Asn Glu Glu Asn Glu Gly Phe Cys Gly Gly Thr Ile Leu Ser Glu
115                 120                 125

Phe Tyr Ile Leu Thr Ala Ala His Cys Leu Tyr Gln Ala Lys Arg Phe
130                 135                 140

Lys Val Arg Val Gly Asp Arg Asn Thr Glu Gln Glu Glu Gly Gly Glu
145                 150                 155                 160

Ala Val His Glu Val Glu Val Val Ile Lys His Asn Arg Phe Thr Lys
                165                 170                 175

Glu Thr Tyr Asp Phe Asp Ile Ala Val Leu Arg Leu Lys Thr Pro Ile
            180                 185                 190

Thr Phe Arg Met Asn Val Ala Pro Ala Cys Leu Pro Glu Arg Asp Trp
        195                 200                 205

Ala Glu Ser Thr Leu Met Thr Gln Lys Thr Gly Ile Val Ser Gly Phe
210                 215                 220

Gly Arg Thr His Glu Lys Gly Arg Gln Ser Thr Arg Leu Lys Met Leu
225                 230                 235                 240

Glu Val Pro Tyr Val Asp Arg Asn Ser Cys Lys Leu Ser Ser Ser Phe
                245                 250                 255

Ile Ile Thr Gln Asn Met Phe Cys Ala Gly Tyr Asp Thr Lys Gln Glu
            260                 265                 270

Asp Ala Cys Gln Gly Asp Ser Gly Gly Pro His Val Thr Arg Phe Lys
        275                 280                 285

Asp Thr Tyr Phe Val Thr Gly Ile Val Ser Trp Gly Glu Gly Cys Ala
    290                 295                 300

Arg Lys Gly Lys Tyr Gly Ile Tyr Thr Lys Val Thr Ala Phe Leu Lys
305                 310                 315                 320

Trp Ile Asp Arg Ser Met Lys Thr Arg Gly Leu Pro Lys Ala Lys Ser
                325                 330                 335

His Ala Pro Glu Val Ile Thr Ser Ser Pro Leu Lys
            340                 345

<210> SEQ ID NO 6
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

```
Pro Tyr Pro Cys Gly Lys Gln Thr Leu Glu Arg Ile Val Gly Gly Gln
    130                 135                 140
Glu Cys Lys Asp Gly Glu Cys Pro Trp Gln Ala Leu Leu Ile Asn Glu
145                 150                 155                 160
Glu Asn Glu Gly Phe Cys Gly Gly Thr Ile Leu Ser Glu Phe Tyr Ile
                165                 170                 175
Leu Thr Ala Ala His Cys Leu Tyr Gln Ala Lys Arg Phe Lys Val Arg
            180                 185                 190
Val Gly Asp Arg Asn Thr Glu Gln Glu Glu Gly Gly Glu Ala Val His
        195                 200                 205
Glu Val Glu Val Val Ile Lys His Asn Arg Phe Thr Lys Glu Thr Tyr
210                 215                 220
Asp Phe Asp Ile Ala Val Leu Arg Leu Lys Thr Pro Ile Thr Phe Arg
225                 230                 235                 240
Met Asn Val Ala Pro Ala Cys Leu Pro Glu Arg Asp Trp Ala Glu Ser
                245                 250                 255
Thr Leu Met Thr Gln Lys Thr Gly Ile Val Ser Gly Phe Gly Arg Thr
            260                 265                 270
His Glu Lys Gly Arg Gln Ser Thr Arg Leu Lys Met Leu Glu Val Pro
        275                 280                 285
Tyr Val Asp Arg Asn Ser Cys Lys Leu Ser Ser Ser Phe Ile Ile Thr
290                 295                 300
Gln Asn Met Phe Cys Ala Gly Tyr Asp Thr Lys Gln Glu Asp Ala Cys
305                 310                 315                 320
Gln Gly Asp Ser Gly Gly Pro His Val Thr Arg Phe Lys Asp Thr Tyr
                325                 330                 335
Phe Val Thr Gly Ile Val Ser Trp Gly Glu Gly Cys Ala Arg Lys Gly
            340                 345                 350
Lys Tyr Gly Ile Tyr Thr Lys Val Thr Ala Phe Leu Lys Trp Ile Asp
        355                 360                 365
Arg Ser Met Lys Thr Arg Gly Leu Pro Lys Ala Lys Ser His Ala Pro
370                 375                 380
Glu Val Ile Thr Ser Ser Pro Leu Lys
385                 390

<210> SEQ ID NO 7
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(7)
<223> OTHER INFORMATION: Gamma-Carboxyglutamic acid
<220> FEATURE:
<221> NAME/KEY: MOD_RES
<222> LOCATION: (14)..(14)
<223> OTHER INFORMATION: Gamma-Carboxyglutamic acid
<220> FEATURE:
<221> NAME/KEY: MOD_RES
<222> LOCATION: (16)..(16)
<223> OTHER INFORMATION: Gamma-Carboxyglutamic acid
<220> FEATURE:
<221> NAME/KEY: MOD_RES
<222> LOCATION: (19)..(20)
<223> OTHER INFORMATION: Gamma-Carboxyglutamic acid
<220> FEATURE:
<221> NAME/KEY: MOD_RES
<222> LOCATION: (25)..(26)
```

```
<223> OTHER INFORMATION: Gamma-Carboxyglutamic acid
<220> FEATURE:
<221> NAME/KEY: MOD_RES
<222> LOCATION: (29)..(29)
<223> OTHER INFORMATION: Gamma-Carboxyglutamic acid
<220> FEATURE:
<221> NAME/KEY: MOD_RES
<222> LOCATION: (32)..(32)
<223> OTHER INFORMATION: Gamma-Carboxyglutamic acid
<220> FEATURE:
<221> NAME/KEY: MOD_RES
<222> LOCATION: (39)..(39)
<223> OTHER INFORMATION: Gamma-Carboxyglutamic acid

<400> SEQUENCE: 7

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Ile Val Gly Gly Gln
    130                 135                 140

Glu Cys Lys Asp Gly Glu Cys Pro Trp Gln Ala Leu Leu Ile Asn Glu
145                 150                 155                 160

Glu Asn Glu Gly Phe Cys Gly Gly Thr Ile Leu Ser Glu Phe Tyr Ile
                165                 170                 175

Leu Thr Ala Ala His Cys Leu Tyr Gln Ala Lys Arg Phe Lys Val Arg
            180                 185                 190

Val Gly Asp Arg Asn Thr Glu Gln Glu Glu Gly Gly Glu Ala Val His
        195                 200                 205

Glu Val Glu Val Val Ile Lys His Asn Arg Phe Thr Lys Glu Thr Tyr
    210                 215                 220

Asp Phe Asp Ile Ala Val Leu Arg Leu Lys Thr Pro Ile Thr Phe Arg
225                 230                 235                 240

Met Asn Val Ala Pro Ala Cys Leu Pro Glu Arg Asp Trp Ala Glu Ser
                245                 250                 255

Thr Leu Met Thr Gln Lys Thr Gly Ile Val Ser Gly Phe Gly Arg Thr
            260                 265                 270

His Glu Lys Gly Arg Gln Ser Thr Arg Leu Lys Met Leu Glu Val Pro
        275                 280                 285

Tyr Val Asp Arg Asn Ser Cys Lys Leu Ser Ser Phe Ile Ile Thr
    290                 295                 300

Gln Asn Met Phe Cys Ala Gly Tyr Asp Thr Lys Gln Glu Asp Ala Cys
305                 310                 315                 320

Gln Gly Asp Ser Gly Gly Pro His Val Thr Arg Phe Lys Asp Thr Tyr
                325                 330                 335
```

```
Phe Val Thr Gly Ile Val Ser Trp Gly Glu Gly Cys Ala Arg Lys Gly
                340                 345                 350

Lys Tyr Gly Ile Tyr Thr Lys Val Thr Ala Phe Leu Lys Trp Ile Asp
            355                 360                 365

Arg Ser Met Lys Thr Arg Gly Leu Pro Lys Ala Lys Ser His Ala Pro
        370                 375                 380

Glu Val Ile Thr Ser Ser Pro Leu Lys
385                 390
```

<210> SEQ ID NO 8
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(7)
<223> OTHER INFORMATION: Gamma-Carboxyglutamic acid
<220> FEATURE:
<221> NAME/KEY: MOD_RES
<222> LOCATION: (14)..(14)
<223> OTHER INFORMATION: Gamma-Carboxyglutamic acid
<220> FEATURE:
<221> NAME/KEY: MOD_RES
<222> LOCATION: (16)..(16)
<223> OTHER INFORMATION: Gamma-Carboxyglutamic acid
<220> FEATURE:
<221> NAME/KEY: MOD_RES
<222> LOCATION: (19)..(20)
<223> OTHER INFORMATION: Gamma-Carboxyglutamic acid
<220> FEATURE:
<221> NAME/KEY: MOD_RES
<222> LOCATION: (25)..(26)
<223> OTHER INFORMATION: Gamma-Carboxyglutamic acid
<220> FEATURE:
<221> NAME/KEY: MOD_RES
<222> LOCATION: (29)..(29)
<223> OTHER INFORMATION: Gamma-Carboxyglutamic acid
<220> FEATURE:
<221> NAME/KEY: MOD_RES
<222> LOCATION: (32)..(32)
<223> OTHER INFORMATION: Gamma-Carboxyglutamic acid
<220> FEATURE:
<221> NAME/KEY: MOD_RES
<222> LOCATION: (39)..(39)
<223> OTHER INFORMATION: Gamma-Carboxyglutamic acid

<400> SEQUENCE: 8

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125
```

```
                Pro Tyr Pro Cys Gly Lys Gln Thr Leu Glu Arg
                    130                 135
```

<210> SEQ ID NO 9
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250
```

<210> SEQ ID NO 10
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (280)..(280)
<223> OTHER INFORMATION: Dehydroalanine

<400> SEQUENCE: 10

```
Lys Asp Gly Asp Gln Cys Glu Thr Ser Pro Cys Gln Asn Gln Gly Lys
1               5                   10                  15
```

Cys Lys Asp Gly Leu Gly Glu Tyr Thr Cys Thr Cys Leu Glu Gly Phe
            20                  25                  30

Glu Gly Lys Asn Cys Glu Leu Phe Thr Arg Lys Leu Cys Ser Leu Asp
        35                  40                  45

Asn Gly Asp Cys Asp Gln Phe Cys His Glu Gln Asn Ser Val Val
    50                  55                  60

Cys Ser Cys Ala Arg Gly Tyr Thr Leu Ala Asp Asn Gly Lys Ala Cys
65                  70                  75                  80

Ile Pro Thr Gly Pro Tyr Pro Cys Gly Lys Gln Thr Leu Glu Arg Ile
                85                  90                  95

Val Gly Gly Gln Glu Cys Lys Asp Gly Glu Cys Pro Trp Gln Ala Leu
            100                 105                 110

Leu Ile Asn Glu Glu Asn Glu Gly Phe Cys Gly Gly Thr Ile Leu Ser
        115                 120                 125

Glu Phe Tyr Ile Leu Thr Ala Ala His Cys Leu Tyr Gln Ala Lys Arg
130                 135                 140

Phe Lys Val Arg Val Gly Asp Arg Asn Thr Glu Gln Glu Glu Gly Gly
145                 150                 155                 160

Glu Ala Val His Glu Val Glu Val Val Ile Lys His Asn Arg Phe Thr
                165                 170                 175

Lys Glu Thr Tyr Asp Phe Asp Ile Ala Val Leu Arg Leu Lys Thr Pro
            180                 185                 190

Ile Thr Phe Arg Met Asn Val Ala Pro Ala Cys Leu Pro Glu Arg Asp
        195                 200                 205

Trp Ala Glu Ser Thr Leu Met Thr Gln Lys Thr Gly Ile Val Ser Gly
210                 215                 220

Phe Gly Arg Thr His Glu Lys Gly Arg Gln Ser Thr Arg Leu Lys Met
225                 230                 235                 240

Leu Glu Val Pro Tyr Val Asp Arg Asn Ser Cys Lys Leu Ser Ser Ser
                245                 250                 255

Phe Ile Ile Thr Gln Asn Met Phe Cys Ala Gly Tyr Asp Thr Lys Gln
            260                 265                 270

Glu Asp Ala Cys Gln Gly Asp Ala Gly Gly Pro His Val Thr Arg Phe
        275                 280                 285

Lys Asp Thr Tyr Phe Val Thr Gly Ile Val Ser Trp Gly Glu Gly Cys
290                 295                 300

Ala Arg Lys Gly Lys Tyr Gly Ile Tyr Thr Lys Val Thr Ala Phe Leu
305                 310                 315                 320

Lys Trp Ile Asp Arg Ser Met Lys Thr Arg Gly Leu Pro Lys Ala Lys
                325                 330                 335

Ser His Ala Pro Glu Val Ile Thr Ser Ser Pro Leu Lys
            340                 345

<210> SEQ ID NO 11
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Glu Gly Phe Glu

```
            20                  25                  30
Gly Lys Asn Cys Glu Leu Phe Thr Arg Lys Leu Cys Ser Leu Asp Asn
             35                  40                  45

Gly Asp Cys Asp Gln Phe Cys His Glu Glu Gln Asn Ser Val Val Cys
 50                  55                  60

Ser Cys Ala Arg Gly Tyr Thr Leu Ala Asp Asn Gly Lys Ala Cys Ile
 65                  70                  75                  80

Pro Thr Gly Pro Tyr Pro Cys Gly Lys Gln Thr Leu Glu Arg Ile Val
                 85                  90                  95

Gly Gly Gln Glu Cys Lys Asp Gly Glu Cys Pro Trp Gln Ala Leu Leu
            100                 105                 110

Ile Asn Glu Glu Asn Glu Gly Phe Cys Gly Gly Thr Ile Leu Ser Glu
            115                 120                 125

Phe Tyr Ile Leu Thr Ala Ala His Cys Leu Tyr Gln Ala Lys Arg Phe
        130                 135                 140

Lys Val Arg Val Gly Asp Arg Asn Thr Glu Gln Glu Glu Gly Gly Glu
145                 150                 155                 160

Ala Val His Glu Val Glu Val Val Ile Lys His Asn Arg Phe Thr Lys
                165                 170                 175

Glu Thr Tyr Asp Phe Asp Ile Ala Val Leu Arg Leu Lys Thr Pro Ile
            180                 185                 190

Thr Phe Arg Met Asn Val Ala Pro Ala Cys Leu Pro Glu Arg Asp Trp
        195                 200                 205

Ala Glu Ser Thr Leu Met Thr Gln Lys Thr Gly Ile Val Ser Gly Phe
    210                 215                 220

Gly Arg Thr His Glu Lys Gly Arg Gln Ser Thr Arg Leu Lys Met Leu
225                 230                 235                 240

Glu Val Pro Tyr Val Asp Arg Asn Ser Cys Lys Leu Ser Ser Ser Phe
                245                 250                 255

Ile Ile Thr Gln Asn Met Phe Cys Ala Gly Tyr Asp Thr Lys Gln Glu
            260                 265                 270

Asp Ala Cys Gln Gly Asp Ala Gly Gly Pro His Val Thr Arg Phe Lys
        275                 280                 285

Asp Thr Tyr Phe Val Thr Gly Ile Val Ser Trp Gly Glu Gly Cys Ala
    290                 295                 300

Arg Lys Gly Lys Tyr Gly Ile Tyr Thr Lys Val Thr Ala Phe Leu Lys
305                 310                 315                 320

Trp Ile Asp Arg Ser Met Lys Thr Arg Gly Leu Pro Lys Ala Lys Ser
                325                 330                 335

His Ala Pro Glu Val Ile Thr Ser Ser Pro Leu Lys
            340                 345

<210> SEQ ID NO 12
<211> LENGTH: 371
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Asn Ser Phe Leu Phe Trp Asn Lys Tyr Lys Asp Gly Asp Gln Cys
1               5                  10                  15

Glu Thr Ser Pro Cys Gln Asn Gln Gly Lys Cys Lys Asp Gly Leu Gly
            20                  25                  30
```

Glu Tyr Thr Cys Thr Cys Leu Glu Gly Phe Glu Gly Lys Asn Cys Glu
            35                  40                  45

Leu Phe Thr Arg Lys Leu Cys Ser Leu Asp Asn Gly Asp Cys Asp Gln
 50                  55                  60

Phe Cys His Glu Glu Gln Asn Ser Val Val Cys Ser Cys Ala Arg Gly
 65                  70                  75                  80

Tyr Thr Leu Ala Asp Asn Gly Lys Ala Cys Ile Pro Thr Gly Pro Tyr
                 85                  90                  95

Pro Cys Gly Lys Gln Thr Leu Glu Arg Leu Ile Asn Lys Glu Arg Arg
            100                 105                 110

Lys Arg Arg Lys Arg Ile Val Gly Gly Gln Glu Cys Lys Asp Gly Glu
            115                 120                 125

Cys Pro Trp Gln Ala Leu Leu Ile Asn Glu Glu Asn Glu Gly Phe Cys
        130                 135                 140

Gly Gly Thr Ile Leu Ser Glu Phe Tyr Ile Leu Thr Ala Ala His Cys
145                 150                 155                 160

Leu Tyr Gln Ala Lys Arg Phe Lys Val Arg Val Gly Asp Arg Asn Thr
                165                 170                 175

Glu Gln Glu Glu Gly Gly Glu Ala Val His Glu Val Glu Val Val Ile
            180                 185                 190

Lys His Asn Arg Phe Thr Lys Glu Thr Tyr Asp Phe Asp Ile Ala Val
        195                 200                 205

Leu Arg Leu Lys Thr Pro Ile Thr Phe Arg Met Asn Val Ala Pro Ala
210                 215                 220

Cys Leu Pro Glu Arg Asp Trp Ala Glu Ser Thr Leu Met Thr Gln Lys
225                 230                 235                 240

Thr Gly Ile Val Ser Gly Phe Gly Arg Thr His Glu Lys Gly Arg Gln
                245                 250                 255

Ser Thr Arg Leu Lys Met Leu Glu Val Pro Tyr Val Asp Arg Asn Ser
            260                 265                 270

Cys Lys Leu Ser Ser Ser Phe Ile Ile Thr Gln Asn Met Phe Cys Ala
        275                 280                 285

Gly Tyr Asp Thr Lys Gln Glu Asp Ala Cys Gln Gly Asp Ala Gly Gly
290                 295                 300

Pro His Val Thr Arg Phe Lys Asp Thr Tyr Phe Val Thr Gly Ile Val
305                 310                 315                 320

Ser Trp Gly Glu Gly Cys Ala Arg Lys Gly Lys Tyr Gly Ile Tyr Thr
                325                 330                 335

Lys Val Thr Ala Phe Leu Lys Trp Ile Asp Arg Ser Met Lys Thr Arg
            340                 345                 350

Gly Leu Pro Lys Ala Lys Ser His Ala Pro Glu Val Ile Thr Ser Ser
        355                 360                 365

Pro Leu Lys
   370

<210> SEQ ID NO 13
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Asn Ser Phe Leu Phe Trp Asn Lys Tyr Lys Asp Gly Asp Gln Cys
 1               5                  10                  15

```
Glu Thr Ser Pro Cys Gln Asn Gln Gly Lys Cys Lys Asp Gly Leu Gly
         20                  25                  30

Glu Tyr Thr Cys Thr Cys Leu Glu Gly Phe Glu Gly Lys Asn Cys Glu
         35                  40                  45

Leu Phe Thr Arg Lys Leu Cys Ser Leu Asp Asn Gly Asp Cys Asp Gln
 50                  55                  60

Phe Cys His Glu Glu Gln Asn Ser Val Val Cys Ser Cys Ala Arg Gly
 65                  70                  75                  80

Tyr Thr Leu Ala Asp Asn Gly Lys Ala Cys Ile Pro Thr Gly Pro Tyr
                 85                  90                  95

Pro Cys Gly Lys Gln Thr Leu Glu Arg Ile Val Gly Gly Gln Glu Cys
            100                 105                 110

Lys Asp Gly Glu Cys Pro Trp Gln Ala Leu Leu Ile Asn Glu Glu Asn
        115                 120                 125

Glu Gly Phe Cys Gly Gly Thr Ile Leu Ser Glu Phe Tyr Ile Leu Thr
130                 135                 140

Ala Ala His Cys Leu Tyr Gln Ala Lys Arg Phe Lys Val Arg Val Gly
145                 150                 155                 160

Asp Arg Asn Thr Glu Gln Glu Glu Gly Gly Glu Ala Val His Glu Val
                165                 170                 175

Glu Val Val Ile Lys His Asn Arg Phe Thr Lys Glu Thr Tyr Asp Phe
            180                 185                 190

Asp Ile Ala Val Leu Arg Leu Lys Thr Pro Ile Thr Phe Arg Met Asn
        195                 200                 205

Val Ala Pro Ala Cys Leu Pro Glu Arg Asp Trp Ala Glu Ser Thr Leu
210                 215                 220

Met Thr Gln Lys Thr Gly Ile Val Ser Gly Phe Gly Arg Thr His Glu
225                 230                 235                 240

Lys Gly Arg Gln Ser Thr Arg Leu Lys Met Leu Glu Val Pro Tyr Val
                245                 250                 255

Asp Arg Asn Ser Cys Lys Leu Ser Ser Ser Phe Ile Ile Thr Gln Asn
            260                 265                 270

Met Phe Cys Ala Gly Tyr Asp Thr Lys Gln Glu Asp Ala Cys Gln Gly
        275                 280                 285

Asp Ala Gly Gly Pro His Val Thr Arg Phe Lys Asp Thr Tyr Phe Val
290                 295                 300

Thr Gly Ile Val Ser Trp Gly Glu Gly Cys Ala Arg Lys Gly Lys Tyr
305                 310                 315                 320

Gly Ile Tyr Thr Lys Val Thr Ala Phe Leu Lys Trp Ile Asp Arg Ser
                325                 330                 335

Met Lys Thr Arg Gly Leu Pro Lys Ala Lys Ser His Ala Pro Glu Val
            340                 345                 350

Ile Thr Ser Ser Pro Leu Lys
        355

<210> SEQ ID NO 14
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Asn Ser Phe Leu Phe Trp Asn Lys Tyr Lys Asp Gly Asp Gln Cys
```

```
                1               5                   10                  15
            Glu Thr Ser Pro Cys Gln Asn Gln Gly Lys Cys Lys Asp Gly Leu Gly
                            20                  25                  30

Glu Tyr Thr Cys Thr Cys Leu Glu Gly Phe Glu Gly Lys Asn Cys Glu
                            35                  40                  45

Leu Phe Thr Arg Lys Leu Cys Ser Leu Asp Asn Gly Asp Cys Asp Gln
                50                      55                  60

Phe Cys His Glu Glu Gln Asn Ser Val Val Cys Ser Cys Ala Arg Gly
            65                      70                  75                  80

Tyr Thr Leu Ala Asp Asn Gly Lys Ala Cys Ile Pro Thr Gly Pro Tyr
                            85                  90                  95

Pro Cys Gly Lys Gln Thr Leu Glu Arg
                            100                 105

<210> SEQ ID NO 15
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
                20                  25                  30

Ser Glu Phe Tyr Ile Leu Thr Ala Ala His Cys Leu Tyr Gln Ala Lys
            35                  40                  45

Arg Phe Lys Val Arg Val Gly Asp Arg Asn Thr Glu Gln Glu Glu Gly
        50                  55                  60

Gly Glu Ala Val His Glu Val Glu Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250
```

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Glu Met Lys Lys Gly His Leu Glu Arg Glu Cys Met Glu Glu Thr
1               5                   10                  15

Cys Ser Tyr Glu Glu Ala Arg Glu Val Phe Glu Asp Ser Asp Lys Thr
            20                  25                  30

Asn Glu

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Lys Arg Arg Lys Arg
1               5

<210> SEQ ID NO 18
<211> LENGTH: 1218
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atggggcgcc cactgcacct cgtcctgctc agtgcctccc tggctggcct cctgctgctc      60
ggggaaagtc tgttcatccg cagggagcag gccaacaaca tcctggcgag ggtcacgagg     120
gccaattcct ttcttttctg gaataaatac aaagatggcg accagtgtga gaccagtcct     180
tgccagaacc agggcaaatg taaagacggc ctcgggaat acacctgcac ctgtttagaa      240
ggattcgaag gcaaaaactg tgaattattc acacggaagc tctgcagcct ggacaacggg     300
gactgtgacc agttctgcca cgaggaacag aactctgtgg tgtgctcctg cgcccgcggg     360
tacacccctg gctgacaacgg caaggcctgc attcccacag gccctaccc ctgtgggaaa     420 cagaccctgg aacgcaggaa gaggaggaag aggatcgtgg gaggccagga atgcaaggac     480
ggggagtgtc cctggcaggc cctgctcatc aatgaggaaa acgagggttt ctgtggtgga     540
accattctga gcgagttcta catcctaacg gcagcccact gtctctacca agccaagaga     600
ttcaaggtga gggtagggga ccggaacacg agcaggagg agggcggtga ggcggtgcac     660
gaggtggagg tggtcatcaa gcacaaccgg ttcacaaagg agacctatga cttcgacatc     720
gccgtgctcc ggctcaagac ccccatcacc ttccgcatga acgtggcgcc tgcctgcctc     780
cccgagcgtg actgggccga gtccacgctg atgacgcaga gacgggat gtgagcggc       840 ttcgggcgca cccacgagaa gggccggcag tccaccaggc tcaagatgct ggaggtgccc     900
tacgtggacc gcaacagctg caagctgtcc agcagcttca tcatcccca gaacatgttc     960 tgtgccggct acgacaccaa gcaggaggat gcctgccagg ggacgcagg ggcccgcac     1020 gtcacccgct tcaaggacac ctacttcgtg acaggcatcg tcagctgggg agagggctgt    1080

| | | |
|---|---|---|
| gcccgtaagg ggaagtacgg gatctacacc aaggtcaccg ccttcctcaa gtggatcgac | 1140 | |
| aggtccatga aaaccagggg cttgcccaag gccaagagcc atgccccgga ggtcataacg | 1200 | |
| tcctctccat taaagtga | 1218 | |

<210> SEQ ID NO 19
<211> LENGTH: 7303
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

| | | |
|---|---|---|
| tctagacaca gtactcggcc acaccatggg gcgcccactg cacctcgtcc tgctcagtgc | 60 | |
| ctccctggct ggcctcctgc tgctcgggga aagtctgttc atccgcaggg agcaggccaa | 120 | |
| caacatcctg gcgagggtca cgagggccaa ttcctttctt ttctggaata aatacaaaga | 180 | |
| tggcgaccag tgtgagacca gtccttgcca gaaccagggc aaatgtaaag acggcctcgg | 240 | |
| ggaatacacc tgcacctgtt tagaaggatt cgaaggcaaa aactgtgaat tattcacacg | 300 | |
| gaagctctgc agcctggaca cggggactg tgaccagttc tgccacgagg aacagaactc | 360 | |
| tgtggtgtgc cctgcgccc gcgggtacac cctggctgac aacggcaagg cctgcattcc | 420 | |
| cacagggccc taccctgtg ggaaacagac cctggaacgc aggaagagga ggaagaggat | 480 | |
| cgtgggaggc caggaatgca aggacgggga gtgtccctgg caggccctgc tcatcaatga | 540 | |
| ggaaaacgag ggtttctgtg gtggaaccat tctgagcgag ttctacatcc taacggcagc | 600 | |
| ccactgtctc taccaagcca agagattcaa ggtgagggta ggggaccgga cacggagca | 660 | |
| ggaggagggc ggtgaggcgg tgcacgaggt ggaggtggtc atcaagcaca ccgttcac | 720 | |
| aaaggagacc tatgacttcg acatcgccgt gctccggctc aagaccccca tcaccttccg | 780 | |
| catgaacgtg gcgcctgcct gcctccccga gcgtgactgg gccgagtcca cgctgatgac | 840 | |
| gcagaagacg gggattgtga gcggcttcgg cgcacccac gagaagggcc ggcagtccac | 900 | |
| caggctcaag atgctggagg tgccctacgt ggaccgcaac agctgcaagc tgtccagcag | 960 | |
| cttcatcatc acccagaaca tgttctgtgc cggctacgac accaagcagg aggatgcctg | 1020 | |
| ccagggggac gcaggggcc cgcacgtcac ccgcttcaag gacacctact cgtgacagg | 1080 | |
| catcgtcagc tggggagagg gctgtgcccg taaggggaag tacgggatct acaccaaggt | 1140 | |
| caccgccttc ctcaagtgga tcgacaggtc catgaaaacc aggggcttgc ccaaggccaa | 1200 | |
| gagccatgcc ccggaggtca taacgtcctc tccattaaag tgagatccca ctcggatccc | 1260 | |
| tattctatag tgtcacctaa atgctagagc tcgctgatca gcctcgactg tgccttctag | 1320 | |
| ttgccagcca tctgttgttt gcccctcccc cgtgccttcc ttgaccctgg aaggtgccac | 1380 | |
| tcccactgtc ctttcctaat aaaatgagga aattgcatcg cattgtctga gtaggtgtca | 1440 | |
| ttctattctg gggggtgggg tgggcagga cagcaagggg gaggattggg aagacaatag | 1500 | |
| caggcatgct ggggatgcgg tgggctctat ggcttctgag gcggaaagaa ccagctgggg | 1560 | |
| ctcgagcggc cgcccccttct gaggcggaaa gaaccagctg tggaatgtgt gtcagttagg | 1620 | |
| gtgtggaaag tccccaggct ccccagcagg cagaagtatg caaagcatgc atctcaatta | 1680 | |
| gtcagcaacc aggtgtggaa agtccccagg ctccccagca ggcagaagta tgcaaagcat | 1740 | |
| gcatctcaat tagtcagcaa ccatagtccc gcccctaact ccgcccatcc cgcccctaac | 1800 | |
| tccgcccagt tccgcccatt ctccgcccca tggctgacta atttttttta tttatgcaga | 1860 | |

```
ggccgaggcc gcctcggcct ctgagctatt ccagaagtag tgaggaggct tttttggagg    1920
cctaggcttt tgcaaaaaag ctagcttccc gctgccatca tggttcgacc attgaactgc    1980
atcgtcgccg tgtcccaaaa tatggggatt ggcaagaacg gagacctacc ctggcctccg    2040
ctcaggaaca gttcaagta cttccaaaga atgaccacaa cctcttcagt ggaaggtaaa     2100
cagaatctgg tgattatggg taggaaaacc tggttctcca ttcctgagaa gaatcgacct    2160
ttaaaggaca gaattaatat agttctcagt agagaactca aagaaccacc acgaggagct    2220
cattttcttg ccaaaagttt ggatgatgcc ttaagactta ttgaacaacc ggaattggca    2280
agtaaagtag acatggtttg gatagtcgga ggcagttctg tttaccagga agccatgaat    2340
caaccaggcc accttagact ctttgtgaca aggatcatgc aggaatttga aagtgacacg    2400
tttttcccag aaaattgattt gggggaaatat aaacttctcc cagaataccc aggcgtcctc   2460
tctgaggtcc aggaggaaaa aggcatcaag tataagtttg aagtctacga gaagaaagac    2520
taacaggaag atgctttcaa gttctctgct cccctcctaa agctatgcat ttttataaga    2580
ccatgggact tttgctggct ttagatcccg cggagatcca gacatgataa gatacattga    2640
tgagtttgga caaaccacaa ctagaatgca gtgaaaaaaa tgctttattt gtgaaatttg    2700
tgatgctatt gctttatttg taaccattat aagctgcaat aaacaagtta acaacaacaa    2760
ttgcattcat tttatgtttc aggttcaggg ggaggtgtgg gaggtttttt aaagcaagta    2820
aaacctctac aaatgtggta tggctgatta tgagctccag cttttgttcc ctttagtgag    2880
ggttaattgc gcgcttggcg taatcatggt catagctgtt tcctgtgtga aattgttatc    2940
cgctcacaat tccacacaac atacgagccg gaagcataaa gtgtaaagcc tggggtgcct    3000
aatgagtgag ctaactcaca ttaattgcgt tgcgctcact gcccgctttc cagtcgggaa    3060
acctgtcgtg ccagctgcat taatgaatcg gccaacgcgc ggggagaggc ggtttgcgta    3120
ttgggcgctc ttccgcttcc tcgctcactg actcgctgcg ctcggtcgtt cggctgcggc    3180
gagcggtatc agctcactca aaggcggtaa tacggttatc cacagaatca ggggataacg    3240
caggaaagaa catgtgagca aaaggccagc aaaaggccag gaaccgtaaa aaggccgcgt    3300
tgctggcgtt tttccatagg ctccgccccc ctgacgagca tcacaaaaat cgacgctcaa    3360
gtcagaggtg gcgaaacccg acaggactat aaagatacca ggcgtttccc cctggaagct    3420
ccctcgtgcg ctctcctgtt ccgaccctgc cgcttaccgg atacctgtcc gcctttctcc    3480
cttcgggaag cgtggcgctt tctcatagct cacgctgtag gtatctcagt tcggtgtagg    3540
tcgttcgctc caagctgggc tgtgtgcacg aaccccccgt tcagcccgac cgctgcgcct    3600
tatccggtaa ctatcgtctt gagtccaacc cggtaagaca cgacttatcg ccactggcag    3660
cagccactgg taacaggatt agcagagcga ggtatgtagg cggtgctaca gagttcttga    3720
agtggtggcc taactacggc tacactagaa ggacagtatt tggtatctgc gctctgctga    3780
agccagttac cttcggaaaa agagttggta gctcttgatc cggcaaacaa accaccgctg    3840
gtagcggtgg tttttttgtt tgcaagcagc agattacgcg cagaaaaaaa ggatctcaag    3900
aagatccttt gatcttttct acggggtctg acgctcagtg gaacgaaaac tcacgttaag    3960
ggattttggt catgagatta tcaaaaagga tcttcaccta gatcctttta aattaaaaat    4020
gaagttttaa atcaatctaa agtatatatg agtaaacttg gtctgacagt taccaatgct    4080
taatcagtga ggcacctatc tcagcgatct gtctatttcg ttcatccata gttgcctgac    4140
tccccgtcgt gtagataact acgatacggg agggcttacc atctggcccc agtgctgcaa    4200
```

```
tgataccgcg agacccacgc tcaccggctc cagatttatc agcaataaac cagccagccg    4260
gaagggccga gcgcagaagt ggtcctgcaa ctttatccgc ctccatccag tctattaatt    4320
gttgccggga agctagagta agtagttcgc cagttaatag tttgcgcaac gttgttgcca    4380
ttgctacagg catcgtggtg tcacgctcgt cgtttggtat ggcttcattc agctccggtt    4440
cccaacgatc aaggcgagtt acatgatccc ccatgttgtg caaaaaagcg gttagctcct    4500
tcggtcctcc gatcgttgtc agaagtaagt tggccgcagt gttatcactc atggttatgg    4560
cagcactgca taattctctt actgtcatgc catccgtaag atgcttttct gtgactggtg    4620
agtactcaac caagtcattc tgagaatagt gtatgcggcg accgagttgc tcttgcccgg    4680
cgtcaatacg ggataatacc gcgccacata gcagaacttt aaaagtgctc atcattggaa    4740
aacgttcttc ggggcgaaaa ctctcaagga tcttaccgct gttgagatcc agttcgatgt    4800
aacccactcg tgcacccaac tgatcttcag catcttttac tttcaccagc gtttctgggt    4860
gagcaaaaac aggaaggcaa aatgccgcaa aaagggaat aagggcgaca cggaaatgtt    4920
gaatactcat actcttcctt tttcaatatt attgaagcat ttatcagggt tattgtctca    4980
tgagcggata catatttgaa tgtatttaga aaaataaaca aataggggtt ccgcgcacat    5040
ttccccgaaa agtgccacct gggaaattgt aaacgttaat attttgttaa aattcgcgtt    5100
aaatttttgt taaatcagct catttttta ccaataggcc gaaatcggca aaatccctta    5160
taaatcaaaa gaatagaccg agatagggtt gagtgttgtt ccagtttgga acaagagtcc    5220
actattaaag aacgtggact ccaacgtcaa agggcgaaaa accgtctatc agggcgatgg    5280
cccactacgt gaaccatcac cctaatcaag ttttttgggg tcgaggtgcc gtaaagcact    5340
aaatcggaac cctaaaggga gcccccgatt tagagcttga cggggaaagc cggcgaacgt    5400
ggcgagaaag gaagggaaga agcgaaagg agcgggcgct agggcgctgg caagtgtagc    5460
ggtcacgctg cgcgtaacca ccacacccgc cgcgcttaat gcgccgctac agggcgcgtc    5520
gcgccattcg ccattcaggc tgcgcaactg ttgggaaggg cgatcggtgc gggcctcttc    5580
gctattacgc cagctggcga aggggggatg tgctgcaagg cgattaagtt gggtaacgcc    5640
agggttttcc cagtcacgac gttgtaaaac gacggccagt gagcgcgcgt aatacgactc    5700
actatagggc gaattggaat taattcgctg gctgagacc cgcagaggaa gacgctctag    5760
ggatttgtcc cggactagcg agatggcaag gctgaggacg ggaggctgat tgagaggcga    5820
aggtacaccc taatctcaat acaacccttg gagctaagcc agcaatggta gagggaagat    5880
tctgcacgtc ccttccaggc ggcctccccg tcaccaccca ccccaacccg ccccgaccgg    5940
agctgagagt aattcataca aaaggactcg cccctgcctt ggggaatccc agggaccgtc    6000
gttaaactcc cactaacgta gaacccagag atcgctgcgt tcccgccccc tcacccgccc    6060
gctctcgtca tcactgaggt ggagaagagc atgcgtgagg ctccggtgcc cgtcagtggg    6120
cagagcgcac atcgcccaca gtccccgaga agttgggggg agggtcggc aattgaaccg    6180 gtgcctagag aaggtggcgc ggggtaaact gggaaagtga tgtcgtgtac tggctccgcc    6240
tttttcccga gggtggggga gaaccgtata taagtgcagt agtcgccgtg aacgttcttt    6300
ttcgcaacgg gtttgccgcc agaacacagg taagtgccgt gtgtggttcc cgcgggcctg    6360
gcctctttac gggttatggc ccttgcgtgc cttgaattac ttccacgccc ctggctgcag    6420
tacgtgattc ttgatcccga gcttcgggtt ggaagtgggt gggagagttc gaggccttgc    6480
gcttaaggag ccccttcgcc tcgtgcttga gttgaggcct ggcttgggcg ctggggccgc    6540
cgcgtgcgaa tctggtggca ccttcgcgcc tatctcgctg ctttcgataa gtctctagcc    6600
```

```
atttaaaatt tttgatgacc tgctgcgacg cttttttct ggcaagatag tcttgtaaat    6660
gcgggccaag atctgcacac tggtatttcg gttttggggg ccgcgggcgg cgacggggcc    6720
cgtgcgtccc agcgcacatg ttcggcgagg cggggcctgc gagcgcggcc accgagaatc    6780
ggacgggggt agtctcaagc tggccggcct gctctggtgc ctggcctcgc gccgccgtgt    6840
atcgccccgc cctgggcggc aaggctggcc cggtcggcac cagttgcgtg agcggaaaga    6900
tggccgcttc ccggccctgc tgcagggagc tcaaaatgga ggacgcggcg ctcgggagag    6960
cgggcgggtg agtcacccac acaaaggaaa agggcctttc cgtcctcagc cgtcgcttca    7020
tgtgactcca cggagtaccg ggcgccgtcc aggcacctcg attagttctc gagcttttgg    7080
agtacgtcgt ctttaggttg gggggagggg ttttatgcga tggagtttcc ccacactgag    7140
tgggtggaga ctgaagttag gccagcttgg cacttgatgt aattctcctt ggaatttgcc    7200 cttttttgagt ttggatcttg gttcattctc aagcctcaga cagtggttca agttttttt    7260 cttccatttc aggtgtcgtg aaaactaccc ctaaaagcca aat    7303

<210> SEQ ID NO 20
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Ile Val Gly Gly Gln Glu Cys
            100                 105                 110

Lys Asp Gly Glu Cys Pro Trp Gln Ala Leu Leu Ile Asn Glu Glu Asn
        115                 120                 125

Glu Gly Phe Cys Gly Gly Thr Ile Leu Ser Glu Phe Tyr Ile Leu Thr
    130                 135                 140

Ala Ala His Cys Leu Tyr Gln Ala Lys Arg Phe Lys Val Arg Val Gly
145                 150                 155                 160

Asp Arg Asn Thr Glu Gln Glu Glu Gly Gly Glu Ala Val His Glu Val
                165                 170                 175

Glu Val Val Ile Lys His Asn Arg Phe Thr Lys Glu Thr Tyr Asp Phe
            180                 185                 190

Asp Ile Ala Val Leu Arg Leu Lys Thr Pro Ile Thr Phe Arg Met Asn
        195                 200                 205

Val Ala Pro Ala Cys Leu Pro Glu Arg Asp Trp Ala Glu Ser Thr Leu
    210                 215                 220

Met Thr Gln Lys Thr Gly Ile Val Ser Gly Phe Gly Arg Thr His Glu
```

```
                225                 230                 235                 240
Lys Gly Arg Gln Ser Thr Arg Leu Lys Met Leu Glu Val Pro Tyr Val
                    245                 250                 255

Asp Arg Asn Ser Cys Lys Leu Ser Ser Ser Phe Ile Ile Thr Gln Asn
                260                 265                 270

Met Phe Cys Ala Gly Tyr Asp Thr Lys Gln Glu Asp Ala Cys Gln Gly
                275                 280                 285

Asp Ala Gly Gly Pro His Val Thr Arg Phe Lys Asp Thr Tyr Phe Val
            290                 295                 300

Thr Gly Ile Val Ser Trp Gly Glu Gly Cys Ala Arg Lys Gly Lys Tyr
305                 310                 315                 320

Gly Ile Tyr Thr Lys Val Thr Ala Phe Leu Lys Trp Ile Asp Arg Ser
                325                 330                 335

Met Lys Thr Arg Gly Leu Pro Lys Ala Lys Ser His Ala Pro Glu Val
                340                 345                 350

Ile Thr Ser Ser Pro Leu Lys
            355

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Asp Gly Asp
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Asp Gly Asp
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Asp Gly Asp
1
```